United States Patent
Yamamoto et al.

(10) Patent No.: US 6,901,926 B2
(45) Date of Patent: Jun. 7, 2005

(54) ULTRASONIC ATOMIZER, ULTRASONIC INHALER AND METHOD OF CONTROLLING SAME

(75) Inventors: Hirohito Yamamoto, Tokyo (JP); Kei Asai, Kyoto (JP)

(73) Assignee: Omron Corporation, Kyoto (JP)

( * ) Notice: Subject to any disclaimer, the term of this patent is extended or adjusted under 35 U.S.C. 154(b) by 7 days.

(21) Appl. No.: 10/624,539

(22) Filed: Jul. 23, 2003

(65) Prior Publication Data

US 2004/0045547 A1 Mar. 11, 2004

Related U.S. Application Data

(62) Division of application No. 08/313,249, filed on Oct. 4, 1994, now Pat. No. 6,651,650.

(30) Foreign Application Priority Data

| Apr. 9, 1992 | (JP) | 4-88463 |
| Apr. 10, 1992 | (JP) | 4-89214 |
| Apr. 10, 1992 | (JP) | 4-90852 |
| Apr. 13, 1992 | (JP) | 4-92649 |
| Apr. 14, 1992 | (JP) | 4-94043 |

(51) Int. Cl.$^7$ .......................................... A61M 11/00
(52) U.S. Cl. .................. 128/200.16; 128/200.18
(58) Field of Search ............... 128/200.16, 200.18; 239/102.2

(56) References Cited

U.S. PATENT DOCUMENTS

| 427,651 A | 5/1890 | Wright |
| 1,215,229 A | 2/1917 | Willson |
| 1,246,682 A | 11/1917 | Thompson |
| 1,463,263 A | 7/1923 | Grayson |
| 1,482,529 A | 2/1924 | Taylor |
| 1,721,381 A | 7/1929 | Ellis |
| 2,559,559 A | 7/1951 | Isenberg |
| 2,744,194 A | * 5/1956 | Auerbach ................ 455/228 |
| 2,855,244 A | * 10/1958 | Camp ..................... 239/102.2 |
| 2,949,900 A | * 8/1960 | Bodine .................... 123/472 |
| 3,103,310 A | * 9/1963 | Lang ........................ 239/4 |
| 3,932,109 A | * 1/1976 | Pitcher et al. .............. 431/1 |

(Continued)

FOREIGN PATENT DOCUMENTS

| CH | 244781 | 4/1947 |
| EP | 0178925 | 4/1986 |

(Continued)

*Primary Examiner*—Aaron J. Lewis
(74) *Attorney, Agent, or Firm*—Morrison & Foerster LLP

(57) ABSTRACT

A bush (31) is fitted into a housing (10) and an ultrasonic pump (12) is supported liquid tightly by the bush (31). The ultrasonic pump (12) is constituted by a pump shaft (21) formed to include a pump bore (22) passing through it axially and having upper and lower ends which are open, and an ultrasonic vibrator (23) mounted on the pump shaft (21) in the vicinity of the midpoint thereof in terms of the axial direction. A liquid vessel.(16) is mounted in the housing (10) in a freely attachable and detachable manner, and the lower end portion of the pump shaft (21) is received inside the liquid vessel (16). A cap (15) is freely detachably attached to the upper end portion of the housing (10) so as to cover the upper end portion of the pump shaft (21). The top side of the cap (15) is provided with a spray port (51), and a step portion (57) is formed for supporting a mesh plate (14) at the periphery thereof at a position below the spray port (51). A compression spring (42) is provided between a portion of the top side of the cap and the mesh plate. The mesh plate (14) is formed to have a multiplicity of minute holes (14a) and is held in pressured contact with the upper end face of the pump shaft (21) by the compression spring (42).

8 Claims, 18 Drawing Sheets

U.S. PATENT DOCUMENTS

| | | | | |
|---|---|---|---|---|
| 4,135,670 | A | 1/1979 | Sugimoto | |
| 4,135,875 | A | 1/1979 | Ballentine | |
| 4,319,716 | A | 3/1982 | Lauer | |
| 4,465,234 | A | 8/1984 | Maehara et al. | |
| 4,533,082 | A * | 8/1985 | Maehara et al. | 239/102.2 |
| 4,541,564 | A | 9/1985 | Berger et al. | |
| 4,642,581 | A | 2/1987 | Erickson | |
| 4,723,708 | A | 2/1988 | Berger et al. | |
| 4,796,807 | A | 1/1989 | Bendig et al. | |
| 4,815,661 | A | 3/1989 | Anthony | |
| 4,850,534 | A | 7/1989 | Takahashi et al. | |
| 4,978,067 | A | 12/1990 | Berger et al. | |
| 5,152,456 | A * | 10/1992 | Ross et al. | 239/102.2 |
| 5,261,601 | A * | 11/1993 | Ross et al. | 239/102.2 |
| 5,297,734 | A * | 3/1994 | Toda | 239/102.2 |
| 5,299,739 | A * | 4/1994 | Takahashi et al. | 239/102.2 |
| 5,312,281 | A * | 5/1994 | Takahashi et al. | 446/25 |
| 5,404,871 | A | 4/1995 | Goodman et al. | |
| 5,586,723 | A * | 12/1996 | Chen et al. | 239/102.2 |
| 5,823,428 | A * | 10/1998 | Humberstone et al. | 239/4 |
| 6,550,691 | B2 * | 4/2003 | Pence | 239/102.2 |
| 6,581,852 | B2 * | 6/2003 | Garcia et al. | 239/326 |
| 6,651,650 | B1 * | 11/2003 | Yamamoto et al. | 128/200.16 |
| 6,732,944 | B2 * | 5/2004 | Litherland et al. | 239/4 |

FOREIGN PATENT DOCUMENTS

| | | |
|---|---|---|
| EP | 0282616 | 9/1988 |
| EP | 0373237 | 6/1990 |
| GB | 2126923 | 4/1984 |
| JP | 59-66380 | 4/1984 |
| JP | 63-38468 | 2/1988 |
| JP | 63-252569 | 10/1988 |
| JP | 28981/1989 | 2/1989 |
| JP | 2-243166 | 9/1990 |
| JP | 15674/1991 | 2/1991 |
| JP | 47063/1991 | 4/1991 |
| SU | 0816471 | 4/1981 |
| SU | 1477420 | 5/1989 |
| WO | 8502346 | 6/1985 |

\* cited by examiner

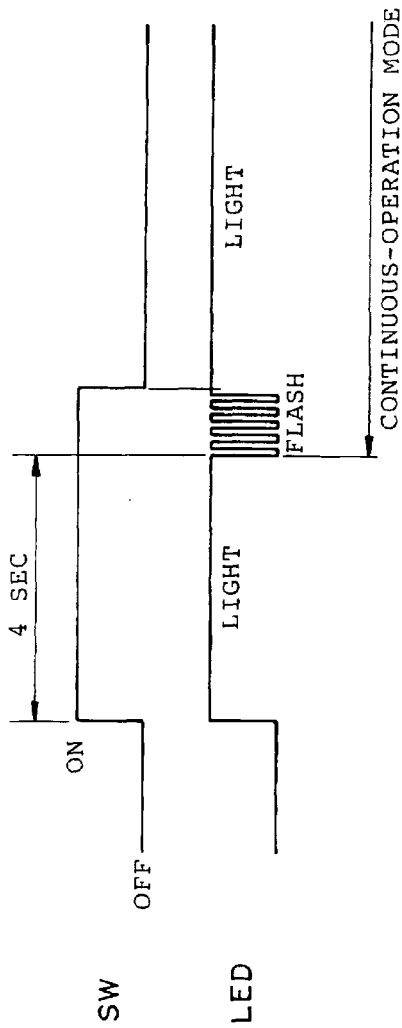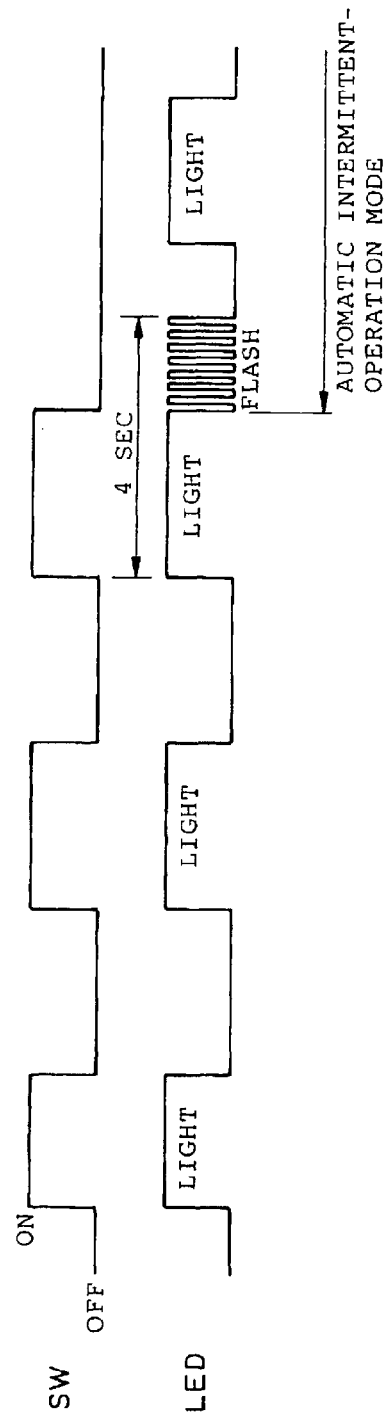

ULTRASONIC ATOMIZER, ULTRASONIC INHALER AND METHOD OF CONTROLLING SAME

TECHNICAL FIELD

This invention relates to an ultrasonic atomizer for pumping up a liquid from a liquid vessel by an ultrasonic pump and atomizing the liquid by passing it through a mesh plate formed to have multiplicity of minute holes, an ultrasonic inhaler serving as one application of the ultrasonic atomizer, and a method of controlling the operation of the inhaler.

BACKGROUND ART

A known example of an ultrasonic atomizer of this type is described in the specification of Japanese Utility Model Application Laid-Open No. 3-15674. The atomizer described in this literature is characterized by use of a mesh plate having tapered minute holes which flare from one side of the plate toward the other. The mesh plate is arranged in such a manner that the side in which the minute holes have the openings of larger diameter opposes the upper end face of the pump shaft of an ultrasonic pump, and such that a minute gap is produced between the mesh plate and the upper end face of the pump shaft.

In an ultrasonic atomizer, it is important to achieve balance between the amount of liquid pumped by the ultrasonic pump and the amount of atomization produced by the mesh plate. When there is a minute gap between the upper end face of the pump shaft and the mesh plate, as in the document mentioned above, the amount of liquid pumped tends to be larger than the amount of liquid atomized. The liquid that is not atomized flows down from the gap to the upper portion (the horn) of the pump shaft and becomes a load on ultrasonic vibration at the horn. This causes an unstable spraying operation and can lead to cessation of operation in some cases.

Another problem is that the user's fingers become soiled when liquid that has not been atomized flows out of the device. An important technical problem is assuring the liquid tightness of the device.

The number of minute holes formed in the mesh plate has a direct influence upon the amount of atomization. The greater the number of minute holes per unit surface area, the greater the amount of atomization. When the number of minute holes is increased, however, there is a decline in the strength of the mesh plate itself. There is a need for some expedient which can provide strength while allowing an increase in the number of minute holes.

Since the mesh plate described in the above-mentioned document is such that the minute holes have aperture diameters that differ on the two sides of the plate, care must be taken in terms of the orientation of these sides when the mesh plate is mounted in the atomizer.

An ultrasonic atomizer can be applied to an ultrasonic inhaler, as set forth above. Medicines of higher cost than inexpensive water and physiologic saline solutions are often used in inhalers. Accordingly, arranging it so that every drop of the medicine is used once the inhaler has been filled is important in terms of economy.

Another requirement of an inhaler is that the user repeat the operation for spraying the inhalant and halt this operation in conformity with breathing. Control of the spraying operation is achieved by having the user turn an operating switch on and off. However, turning the operating switch on and off often is troublesome or difficult particularly for the elderly or children. There is a need to arrange it so that the liquid is sprayed automatically and intermittently in conformity with the user's breathing.

DISCLOSURE OF THE INVENTION

An object of the present invention is to provide a structure in an ultrasonic atomizer which makes it possible to achieve balance between amount of liquid pumped and amount of liquid atomized so that efficient and stable atomization can be obtained.

Another object of the present invention is to facilitate cleaning and replacement of the mesh plate.

A further object of the present invention is to provide a mesh plate having sufficient strength.

Yet another object of the present invention is to increase the amount of atomization by increasing the number of minute holes in the mesh plate.

Another object of the present invention is to improve liquid tightness of the device without limiting the vibration of a horn on the ultrasonic pump.

Another object of the present invention is to provide a structure which will not allow any excess liquid not atomized to flow out of the device.

A further object of the present invention is to enable effective utilization of liquid with which the device has been filled.

A further object of the present invention is to provide an inhaler, as well as a method of controlling the inhaler, in which it is possible to achieve automatic, intermittent spraying that conforms to the breathing of the user.

An ultrasonic atomizer according to the present invention comprises an ultrasonic pump comprising a pump shaft formed to have a pump bore passing through it axially and having open upper and lower ends, and an ultrasonic vibrator mounted on the pump shaft in the vicinity of the midpoint with respect to the axial direction, a liquid vessel provided at a position at which it is penetrated by a lower end of the pump shaft, a mesh plate placed on an upper end face of the pump shaft and formed to have a multiplicity of minute holes, and a biasing resilient member for biasing the mesh plate toward the upper end face of the pump shaft.

The pump shaft also is vibrated in the axial direction by vibration of the ultrasonic vibrator, whereby the liquid inside the liquid vessel is pumped up through the pump bore of the pump shaft. Since the mesh plate is urged against the upper end face of the pump by the resilient member, the mesh plate also vibrates by following up the motion of the pump shaft. Owing to the fact that the mesh plate is vibrated, and by virtue of the fact that the mesh plate is biased by the resilient member, the mesh plate acts as a type of valve which opens and closes the opening at the upper end of the pump bore in the pump shaft. The liquid pumped when the valve is opened is supplied to the mesh plate. When the valve is closed, the liquid is passed through the mesh plate so as to be atomized and sprayed. Since liquid in the amount pumped is atomized, good balance is achieved between the amount of liquid pumped and the amount of liquid atomized, and the spraying operation carried out is efficient and stable.

Since the mesh plate should be brought into pressured contact with the upper end face of the pump shaft at least in the vicinity of the opening at the upper end thereof, it is preferred that the following structure be adopted:

In a preferred embodiment, the upper end face of the pump shaft is formed to have a shape in which the upper end face is slightly and smoothly curved so as to attain maximum height at the position of the opening in the upper end of the pump bore and diminish in height as the periphery is approached.

In case of an arrangement in which the mesh plate is biased by the resilient member at a peripheral edge extending outwardly from the upper end face of the pump shaft, the mesh plate curves slightly. The curvature of the upper end face of the pump shaft, the elastic force of the resilient member and the strength of the mesh plate are decided in such a manner that the degree to which the mesh plate curves is less than the degree of curvature of the upper end face of the pump shaft.

In another embodiment, the upper end face of the pump shaft is formed to have a protuberance which projects in an area that includes the opening in the upper end of the pump bore.

In another embodiment, the mesh plate is formed to have a shape in which the central portion thereof is bent or curved slightly so as to point downward.

In a further embodiment, the biasing resilient member is a compression coil spring having a coil diameter which becomes progressively smaller as the mesh plate is approached, in such a manner that the mesh plate is biased at a position thereof situated on the upper end face of the pump shaft.

As set forth in the above-mentioned document, it is preferred that the mesh plate used be formed in such a manner that the minute holes flare outwardly in the direction extending from the top side to the bottom side of the mesh plate.

An arrangement recommended to heighten the density of the minute holes in the mesh plate is one in which the minute holes are formed at equal intervals long the sides of a multiplicity of regular hexagons whose diagonals vary at fixed distances.

The present invention also provides other improvements relating to the mesh plate. One is a mesh plate in which small areas devoid of the formation of minute holes are present in areas surrounded by minute holes. Since the mesh plate has a multiplicity of minute holes, it is nearly impossible to inspect all of the them. Accordingly, if minute holes to be inspected are specified using the small areas devoid of minute holes as a reference, it becomes possible to inspect minute holes at the same positions at all times.

In another mesh plate, an area devoid of the formation of minute holes is present over a region broader than the opening in the upper end of the pump bore of the pump shaft at a location opposing the opening in the upper end. By virtue of this arrangement, the above-described valve action is attained more effectively.

In yet another mesh plate, cut-outs of different size are formed in the periphery of the mesh plate at least at two locations other than locations having point symmetry about the center of the mesh plate.

The mesh plate is placed upon or attached to the step portion or some other location on a cap, described below. If a mesh-plate supporting member provided on such as a cap is provided with projections that mate with the two cut-outs mentioned above, it will be possible to attach and detach the mesh plate without mistaking the surface orientation of the mesh plate. This is convenient for mesh plates having minute holes whose openings differ in size depending upon the particular side.

In another preferred embodiment of an ultrasonic atomizer according to the present invention, there are further provided a housing, to which the liquid vessel is attached in a freely detachable manner, for supporting the ultrasonic pump, and a cap attached to a portion of the housing in a freely detachable manner so as to cover the upper end of the pump shaft. The top side of the cap is provided with a spray port and a step portion is formed for supporting the mesh plate at the perimeter thereof at a position beneath the spray port. The biasing resilient member is provided between a portion of the top side of the cap and the mesh plate.

When the cap is attached to the housing, the mesh plate is biased by the resilient member and brought into contact with the upper end face of the pump shaft. Thus, positioning of the mesh plate can be achieved with ease. Since the mesh plate is provided on the cap, cleaning or replacement (inclusive of replacement of the cap) is facilitated.

In yet another embodiment, the peripheral portion of the mesh plate is provided with an annular plate, or a spacer is provided between the mesh plate and the upper end face of the pump shaft, in order that the biasing force produced by the biasing member may be applied to the mesh plate uniformly.

The present invention provides a mesh plate having high strength. The mesh plate has two sides overall and is formed to have a multiplicity of minute holes passing through it from one side to the other side. Each minute hole flares outwardly from the one side to the other side, and a single plate-shaped body is deformed continuously at the location of each minute hole in such a manner that a groove or recess is formed between mutually adjacent minute holes on the one side.

The present invention further provides an effective seal structure in an ultrasonic atomizer. Specifically, in an ultrasonic atomizer comprising an ultrasonic pump having a pump shaft formed to have a pump bore passing through it axially and having open upper and lower ends, and an ultrasonic vibrator mounted on the pump shaft in the vicinity of the midpoint with respect to the axial direction, wherein a liquid inside a liquid vessel is pumped up from the lower end of the pump bore and the liquid is supplied to a mesh plate from the upper end of the pump bore so as to be sprayed, the present invention is characterized in that there is provided a bush for encircling and supporting liquid tightly a portion of the pump shaft of the ultrasonic pump excluding upper and lower end portions of the pump shaft, an annular seal lip, in intimate liquid-tight contact with a portion of the pump shaft situated higher than the ultrasonic vibrator, formed integrally at least at two locations, one above the other, on an upper portion of the bush, and a gap provided between the portion of the pump shaft and the bush between the annular seal lips at the at least two locations.

The liquid tightness of the ultrasonic pump within the bush is assured by the annular seal lips. Further, the bush is not made to contact, over its entire surface, the upper portion (horn) of the pump shaft, which undergoes large vibration; only the seal ribs are in partial intimate contact with the upper portion of the pump shaft. As a result, vibration of the horn is not attenuated.

The present invention further provides an ultrasonic atomizer having a reservoir for collecting overflowing liquid not atomized. Specifically, the ultrasonic atomizer according to this aspect of the present invention comprises an ultrasonic pump having a pump shaft formed to have a pump bore passing through it axially and having open upper and lower ends, and an ultrasonic vibrator mounted on the pump shaft in the vicinity of the midpoint with respect to the axial direction, a liquid vessel provided at a position at which it is penetrated by a lower end of the pump shaft, a mesh plate placed on an upper end face of the pump shaft and formed to have a multiplicity of minute holes, a biasing resilient member for biasing the mesh plate toward the upper end face of the pump shaft, a bush for encircling and supporting liquid tightly a portion of the pump shaft of the ultrasonic pump excluding upper and lower end portions of the pump shaft, a housing in which the bush is fitted liquid tightly, and a cap attached in a freely detachable manner to an annular projecting wall, which is formed on the housing about the upper end portion of the pump shaft, so as to cover the upper end portion of the pump shaft, a reservoir being formed with the top side of the bush serving as its bottom surface and at least one of the cap and annular projecting wall serving as its peripheral wall.

Liquid which has flowed into the reservoir is pumped along the pump shaft by the vibration thereof and is eventually atomized. Accordingly, the liquid does not overflow to the exterior of the device and does soil the fingers of the user. In addition, the liquid is used in an effective manner.

The present invention further provides an ultrasonic atomizer in which liquid inside the liquid vessel can be utilized without any being left unused.

The present invention is characterized in that, in an ultrasonic atomizer comprising a liquid vessel accommodating a liquid to be atomized, and an ultrasonic pump having a pump shaft formed to have a pump bore passing through it axially and having open upper and lower ends, and an ultrasonic vibrator mounted on the pump shaft, a lower end of the pump shaft is disposed in close proximity to a bottom surface or side surface of the liquid vessel in such a manner that residual liquid remaining inside the liquid vessel is pumped upon attaching itself to the lower end of the pump shaft by surface tension.

In a preferred embodiment, the liquid vessel is formed to have a recess for collecting the residual liquid remaining inside the liquid vessel, and the lower end of the pump shaft is disposed so as to face the recess.

Even if the amount of liquid remaining in the liquid vessel is small, the liquid attaches itself to the lower end of the pump shaft and is pumped by virtue of surface tension and ultrasonic vibration so that almost all of the liquid is used for spraying purposes. This is particularly effective when a costly medicine is used as the liquid.

Finally, the present invention provides an ultrasonic inhaler, and a method of controlling the same, in which the inhaler has a learning function and spraying is rendered intermittent automatically at a period that substantially coincides with the period at which an operating switch is operated by the user.

Specifically, the present invention provides an ultrasonic inhaler having an ultrasonic pump comprising a pump shaft formed to have a pump bore passing through it axially, and an ultrasonic vibrator mounted on the pump shaft, wherein liquid is pumped through the pump shaft and sprayed by ultrasonic vibration, characterized by comprising a drive circuit for driving the ultrasonic vibrator of the ultrasonic pump, an operating switch, first control means responsive to on/off operation of the operating switch for controlling drive of the ultrasonic vibrator by the drive circuit, and second control means which, in response to the operating switch being turned on and off one time or a plurality of times, is for deciding ON time and OFF time (as by calculating average value) in automatic intermittent operation on the basis of ON time and OFF time of the operating switch, and controlling the drive circuit in such a manner that the ultrasonic vibrator is driven at a period of the ON time and OFF time decided.

In an ultrasonic inhaler having an ultrasonic pump comprising a pump shaft formed to have a pump bore passing through it axially, and an ultrasonic vibrator mounted on the pump shaft, wherein liquid is pumped through the pump shaft and sprayed by the ultrasonic vibrator, a method of controlling the inhaler according to the present invention comprises driving the ultrasonic vibrator during time which an operating switch is ON when the operating switch has been turned on, measuring the on time, halting drive of the ultrasonic vibrator during time which the operating switch is OFF when the operating switch has been turned off, measuring the OFF time, deciding ON time and OFF time in automatic intermittent operation on the basis of the measured ON time and OFF time of the operating switch after the operating switch has been turned on and off a prescribed number of times, and driving the ultrasonic vibrator at a period of the on time and off time decided.

When the user turns the operating switch on and off a number of times in conformity with his or her own respiration, each of the on and off times is measured to decide on and off times suited to the user. The device thereafter enters an automatic intermittent-operation mode in which the spraying operation is performed intermittently at the period of the on and off times decided. This means that the user can breath without operating the operating switch any further.

In an embodiment, the second control means is started so as to perform the automatic intermittent operation in response to on/off operation of the operating switch repeated a requisite plurality of times. Alternatively, the second control means makes a transition to the automatic intermittent operation upon verifying that ON time of the operating switch the last time in the requisite plurality of times is greater than a first prescribed time.

In another embodiment, an automatic intermittent-operation mode switch is provided, the second control means is started so as perform the automatic intermittent operation in response to an input from the automatic intermittent-operation mode switch.

Preferably, third control means is provided for controlling the drive circuit so as to drive the ultrasonic vibrator continuously in response to ON time of the operating switch that is greater than a second predetermined time. As a result, spraying is performed continuously even if the user no longer presses the operating switch.

It is further preferred that a manual mode in which the user operates the operating switch at all times be provided.

Other features and advantages of the present invention will be apparent in the description of an embodiment given with reference to the drawings.

BRIEF DESCRIPTION OF THE DRAWINGS

FIGS. 12a through 12c show another example of a mesh plate, in which FIG. 12a is a plan view, FIG. 12b a sectional view taken along line b—b in FIG. 12a and FIG. 12c a side view;

FIGS. 26a and 26b are time charts showing the on/off operation of an operating switch, the display on a display device and a transition to each operating mode.

BEST MODE FOR CARRYING OUT THE INVENTION

Figure 1:
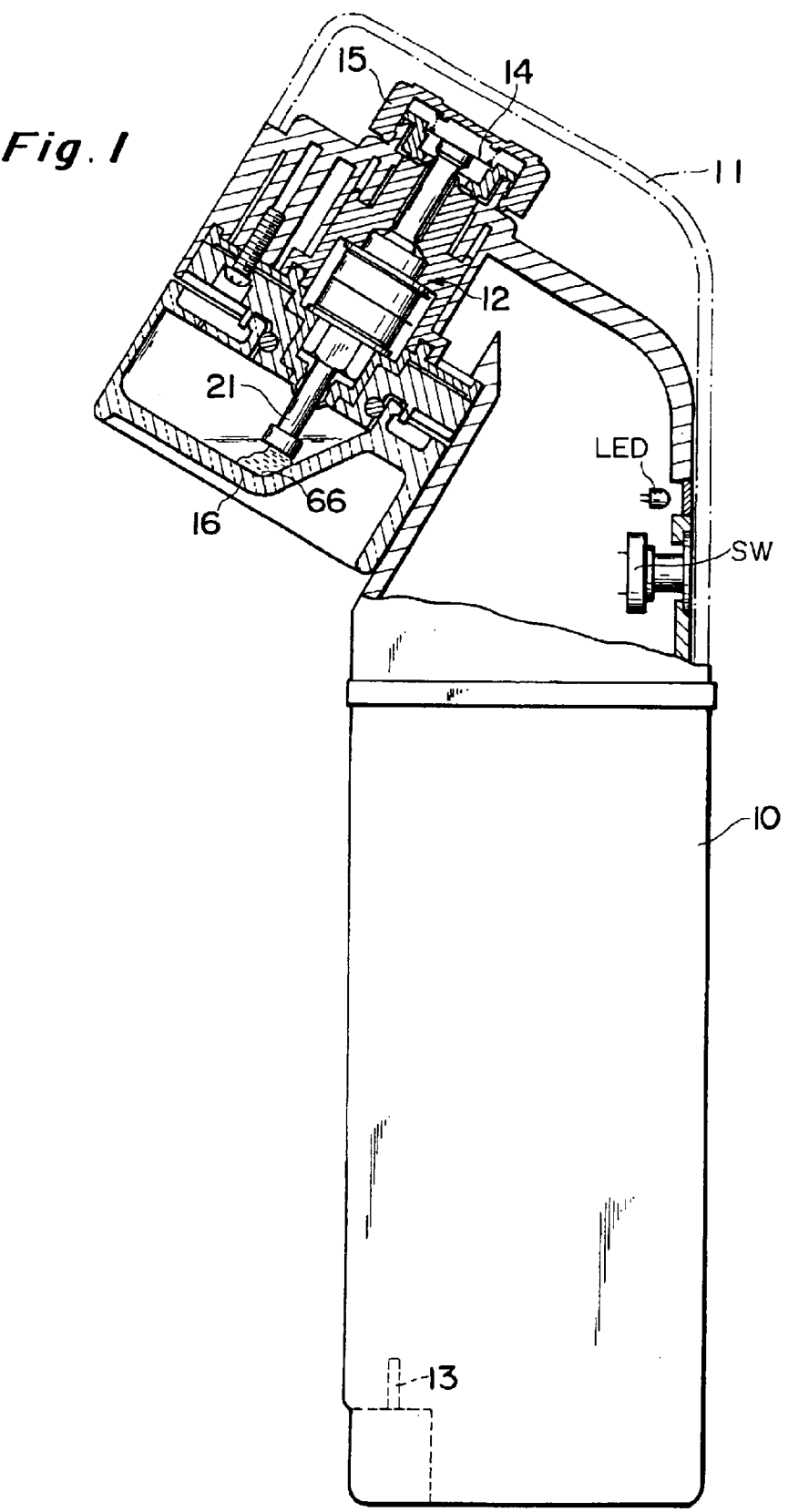
FIG. 1 is a side view, partially cut away, showing the overall construction of an ultrasonic atomizer.

FIG. 1 illustrates the overall construction of an ultrasonic atomizer. In order to facilitate an understanding of the invention, the ultrasonic atomizer is shown somewhat larger than actual size.

The lower half portion of the ultrasonic atomizer extends vertically in the form generally of a rectangle and has a cross section which is nearly a regular square, and the upper half portion is curved upward at an incline so as to point in the forward direction. The upper half portion, especially the uppermost part of the device, is provided with the principal mechanical components such as an ultrasonic pump 12, a mesh plate 14 for atomizing the liquid pumped up by the pump, a cap 15 holding the mesh plate 14, and a liquid vessel 16 accommodating a liquid (medicine or the like). These will be described later. The rear side of the upper half portion of the housing is covered by a freely detachable cover indicated by the chain lines. The cover is detached when the ultrasonic atomizer is used.

Electric circuitry composed of a drive circuit of the ultrasonic pump inclusive of an ultrasonic vibrator circuit, a control circuit having various operating modes, and a power supply circuit is incorporated within the lower half portion of the housing 10. These circuits will be described later. A switch SW operated by the user and a display device (light-emitting diode) LED are provided on the back side of the upper half portion covered by the cover 11. The ultrasonic atomizer has an internal chargeable battery. A jack 13 into which a plug led out from an external AC adapter or the like is plugged in order to charge the battery is provided in a cavity in the lower portion of the housing 10.

Figure 2:
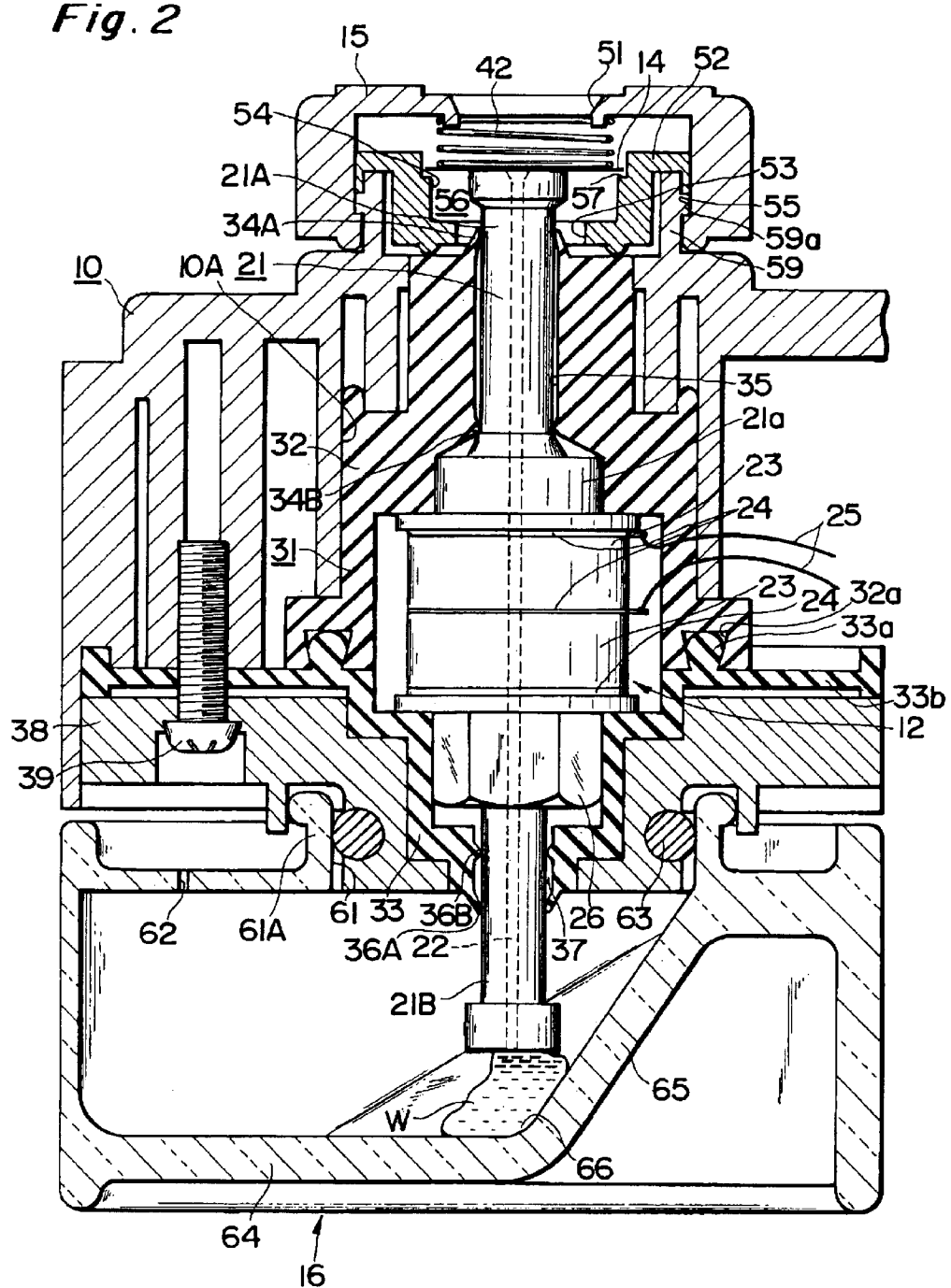
FIG. 2 is an enlarged sectional view showing the principal mechanical construction of the ultrasonic atomizer.

FIG. 2 illustrates, in larger size, the principal mechanical components provided in the upper half portion of the housing 10.

The ultrasonic pump 12 comprises a metallic pump shaft 21 having a small (diameter of not more than 1 mm) pump bore 22 passing through it in the axial direction, and two piezoelectric elements (ultrasonic vibrators) 23 secured to the pump shaft 21 substantially at its midpoint along the length direction thereof. A flange 21a is formed as an integral part of the pump shaft 21 at a portion of the pump shaft 21 somewhat above its midpoint. The piezoelectric elements 23 are annular in shape and are fitted over the pump shaft 21. Annular electrode plates 24 are provided on both sides of the piezoelectric elements 23. A nut 26 is screwed onto male threads formed on the pump shaft 21 so that the piezoelectric elements 23 and electrode plates 24 are firmly secured to the pump shaft 21 between the flange 21a and nut 26. A high-frequency (ultra-high-frequency) voltage from the above-described drive circuit is applied to the electrodes 24 through lead wires 25 so that the piezoelectric elements 23 may vibrate ultrasonically mainly in the axial direction of the pump shaft 21.

A pump bore 22 opens in the lower end face of the pump shaft 21 as well as in the upper end face of the pump shaft 21. A lower end portion 21B of the pump shaft 21 projects into the liquid vessel 16 and is submerged within the liquid inside the vessel 16. The pump shaft 21 has an upper end portion 21A serving as a horn, with the diameter of the upper end being made somewhat larger. The ultrasonic vibration of the piezoelectric elements 23 is transmitted to the pump shaft 21 so that the pump shaft 21 also undergoes ultrasonic vibration in the axial direction, as a result of which the liquid inside the liquid vessel 16 rises within the pump bore 22 of the pump shaft 21. It is believed that this is ascribable to the force applied by the ultrasonic vibration, the surface tension of the liquid and the negative pressure generated inside the pump bore 22.

The above-described ultrasonic pump 12 is encircled by a waterproof bush 31 comprising a resilient body (rubber, for example) and is secured to the upper half portion of the housing 10 via the bush 31.

The bush 31 is constituted by an upper half body 32 and a lower half body 33. A space which accommodates the ultrasonic pump 12 is formed inside the upper half body 32 and lower half body 33. An annular groove 32a is formed in the bottom side of the upper half body 32 and an annular projection 33a is formed in the top side of the lower half body 33. The two bodies 32, 33 are joined to construct the bush 31 by mating the projection 33a with the groove 32a. The upper portion of the lower half body 33 is further formed to have an outwardly extending flange 33b. The upper half body 32 is tightly fitted into an accommodating recess 10A formed in the housing 10. The lower half body 33 is supported inside a recess of a retaining member 38. The latter is secured to the housing 10 at three locations (only one of which is shown) by means of screws 39. Thus, the entire portion of the pump shaft 21, with the exception of an upper end portion 21A and lower end portion 21B thereof, of the ultrasonic pump 12 is covered water tightly by the bush 31, and the pump shaft is secured to the housing 10.

Upper and lower portions of an inner circumferential surface of a cylindrical portion formed on the upper half body 32 of the bush and penetrated by the pump shaft 21 are formed to have inwardly projecting annular seal lips 43A, 43B as integral parts of the upper half body 32 of the bush. The annular seal lips 43A, 43B are in intimate contact with the outer circumferential surface of the pump shaft 21 and maintain liquid tightness. Between the seal lip 43A of the upper portion and the seal lip 43B of the lower portion, a small gap 35 is formed between the inner circumferential surface of the cylindrical portion of the upper half body 32 of the bush and the outer circumferential surface of the pump shaft 21. Since the area of contact between the upper half body 32 of the bush and the upper portion (horn) 21A of the pump shaft 21 is small, ultrasonic vibration of a large amplitude can be obtained at the upper portion of the pump shaft 21. The middle (flange 21a, vibrators 23, nut 26, etc.) of the ultrasonic pump 12 where the amplitude of vibration is small is held tightly by the bush 31.

Similarly, with regard to the lower half body 33 of the bush, upper and lower portions of the inner circumferential surface of a cylindrical portion of the lower half body penetrated by the pump shaft 21 are formed to have inwardly projecting annular seal lips 36B, 36A as integral parts of the lower half body 33. The seal lips 36A, 36B are in intimate contact with the outer circumferential surface of the lower portion of pump shaft 21, whereby liquid tightness is maintained. Further, between the upper and lower seal lips 36B, 36A, a small gap 37 is formed between the lower half body 33 and the pump shaft 21 to assure large ultrasonic vibration.

The periphery of the housing at a position where the upper end portion 21A of the pump shaft 21 protrudes is integrally formed to have a cylindrical portion (annular projection) 59, which is low in height, for the purpose of attaching the cap 15. The outer circumferential portion of the cylindrical portion 59 is formed to have projections 59a at two locations.

The cap 15 is formed to have a spray port 51 in its top side. The bottom side of the cap is open. A base 52 is fitted into the cap 15. The base 52 is formed to have a hole 53 through which the upper end portion of the pump shaft 21 is loosely passed, and the outer side of the base is formed to have an annular groove which receives the cylindrical portion 59. The inner circumferential surface of the cap 15, which is formed by the base 52 and cap 15, is formed to have vertical grooves (not shown in FIG. 2) through which the projections 59a are passed, as well as a groove 55 leading to the upper ends of the vertical grooves and inclined diagonally upward at a slight angle. Accordingly, the cap 15 is secured to the cylindrical portion 59 (this is the state shown in FIG. 2) by placing the cap on the cylindrical portion 59 at a position where the projections 59a coincide with the vertical grooves and then turning the cap 15 slightly, whereby the projections 59a are fitted into the groove 55 and moved into the groove 55. Thus, the cap 15 is capable of being attached to the housing 10 in a freely detachable manner. It goes without saying that the arrangement for attaching the cap 15 to the cylindrical portion 59a is not limited to that described above. The cap can be attached by screws or simply by mating projections with recesses.

The upper portion of the base 52 of cap 15 is further formed to include an annular step 57 at a position facing a recess 54. The mesh plate 14, which is provided with a multiplicity of minute holes, is placed upon the annular step 57. A compression spring 42 is provided between the periphery of the mesh plate 14 and the periphery of the spray port 51 of the cap 15. In a state in which the cap 15 has been detached from the housing 10, the mesh plate 14 is pressed against step 57 at the periphery of the mesh plate by the compression spring 42. When the cap 15 is attached to the cylindrical portion 59 of the housing 10, the upper end face of the pump shaft 21 abuts against the central portion of the mesh plate 14 and the periphery of the mesh plate 14 lifts up slightly from the step 57. The mesh plate 14 is biased in the direction of the upper end face of the pump shaft 21 at all times by the spring 42 so that the mesh plate 14 will vibrate by following up the vertical vibration of the horn 21A. Liquid which has risen through the pump bore 22 of the pump shaft 21 is atomized very finely through the mesh plate 14 and is sprayed to the outside from the spray port 51. The details of the mesh plate 14 as well as the relationship among the mesh plate 14, the spring 42 and the upper end face of the pump shaft 21 will be described in detail later.

The mesh plate 14 is attached to the cap 15. Since the cap 15 is freely attachable and detachable with respect to the housing 10, it is easy to clean or replace the mesh plate 15 (where replacement can mean replacement of the mesh and cap). Further, positional adjustment of the mesh plate 14 relative to the upper end face of the pump shaft 21 is made unnecessary.

A space delimited by the top side of the upper half body 32 of the bush inclusive of the annular seal lip 34A, the outer circumferential surface of the horn 21A, the hole 53 in the base 52 and the recess 54 serves as a liquid reservoir 56. In a case where the amount of liquid pumped to the upper end face of the horn 21A by the ultrasonic pump 12 is greater than the amount of liquid atomized, as a result of which the liquid overflows from the upper end face of the horn 21A, and in a case where the user accidentally allows to drip liquid, any liquid will collect temporarily in the liquid reservoir 56. Owing to the ultrasonic vibration of the horn 21A, however, the liquid is pumped up to the bottom side of the mesh plate 14 and atomized. A decline in atomization performance or instability thereof ascribed to attenuation of the vibrational amplitude of the horn 21A or to some other cause can thus be prevented. Further, since liquid which has overflowed from the upper end face of the horn 21A is prevented from flowing out to the exterior of the housing 10, there is no risk of the user's fingers being soiled and loss of costly medicine can be prevented.

The retaining member 38 projects downwardly in the form of a cylinder from the portion surrounding the lower half body 33 of the bush and the periphery of this cylindrical projection is provided with an O-ring 63. Further, an annular projection 38A is formed on the bottom side of the retaining member 38 on the outer side of the cylindrical projection. The annular projection 38A preferably is partially broken off at a plurality of locations. The liquid vessel 16, meanwhile, is formed from a transparent material. The top side of the vessel has an opening 61 the periphery of which projects slightly in the form of a cylinder (the periphery of the cylindrical opening is indicated at numeral 61A). By inserting the cylindrical periphery 61A of the liquid vessel 16 between the O-ring 63 and the annular projection 38A, the vessel 16 is fixedly attached to the bottom side of the retaining member 38. The liquid vessel may thus be freely attached to and detached from the housing 10. Since the vessel 16 is transparent, the amount of liquid inside can be confirmed visually from the outside. The top side of the vessel 16 is provided with a small hole 62 communicating with the atmosphere. This is to prevent negative pressure from being produced inside the liquid vessel as a result of the liquid in the liquid vessel 16 being pumped by the ultrasonic pump 12. The details of the structure of the vessel 16 and the advantages thereof will be described later.

Figure 3:
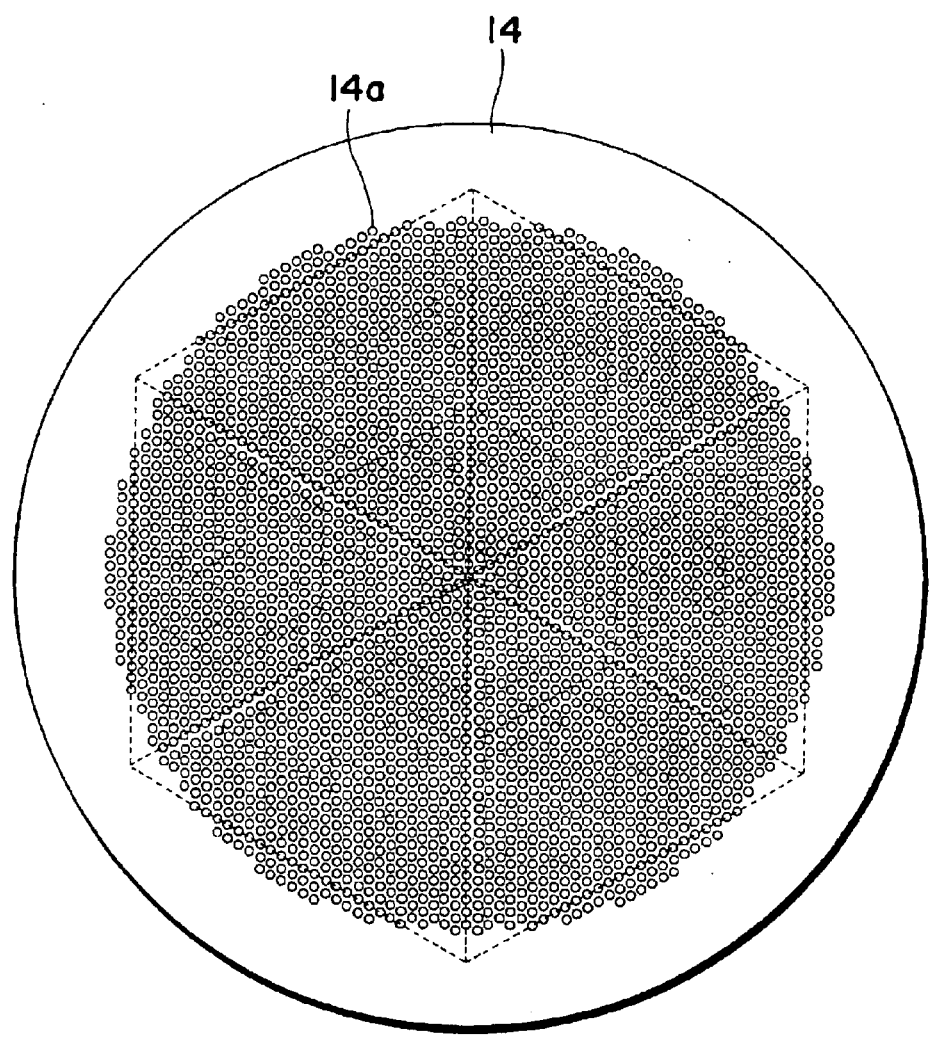
FIG. 3 is an enlarged plan view of a mesh plate.

FIG. 3 is an enlarged plan view of the mesh plate 14. The mesh plate 14 is provided with a multiplicity of minute holes 14a, as mentioned above.

The multiplicity of holes 14a preferably are formed at equal intervals along the sides of a number of regular hexagons drawn with their centers on the center of the circular mesh plate 14, as well as at the apices of the hexagons. The lengths of the diagonals of the number of regular hexagons vary at fixed lengths from one hexagon to the next. The number of minute holes 14a along one side of a regular hexagon differs from the number along one side of the adjacent hexagon by one. If this arrangement is adopted, the number of minute holes 14a per unit area is maximized and the amount of liquid atomized is increased as a result.

Figure 4:
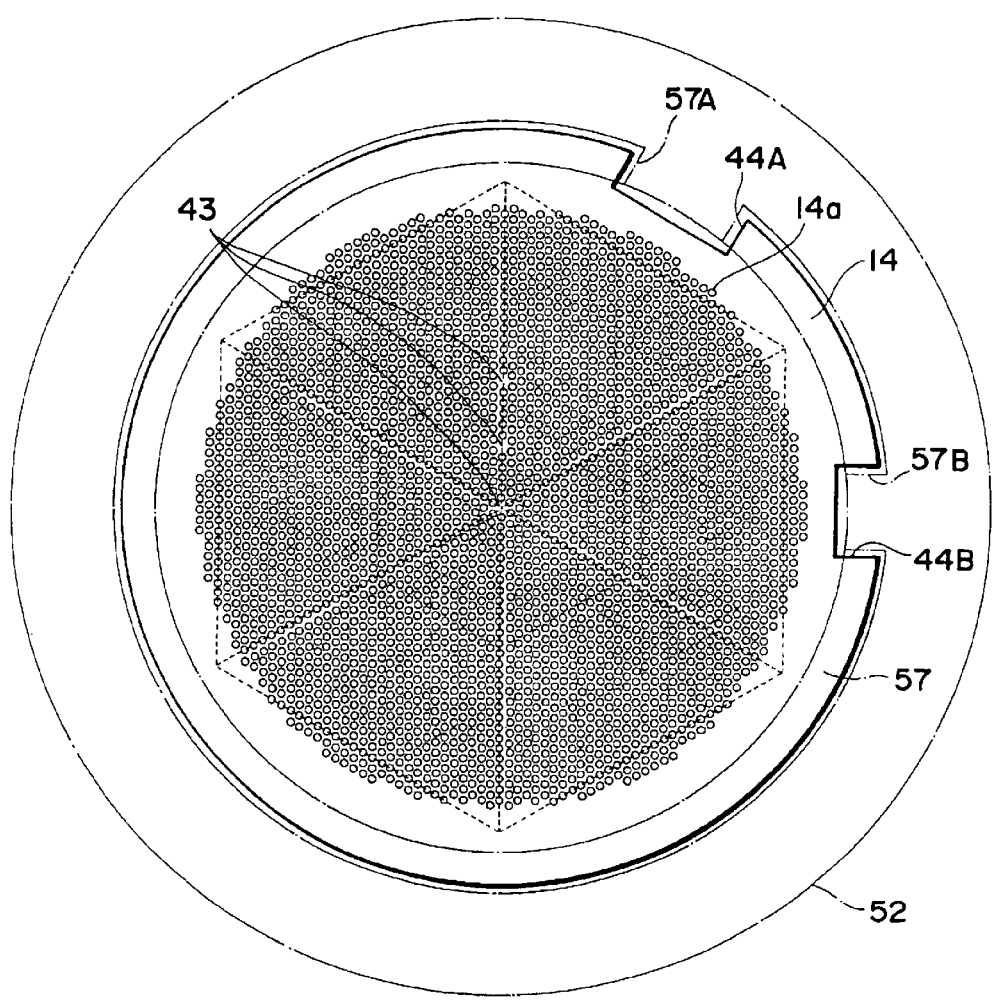
FIG. 4 is an enlarged plan view showing another example of a mesh plate.

FIG. 4 illustrates another example of the mesh plate 14. This mesh plate has two characterized features in addition to those mentioned above.

One feature is that blank portions 43 devoid of the minute holes 14a are provided. There are a total of three blank portions 43 in FIG. 4, namely at a point at the center and at two points established at intervals of five minute holes from the center along one portion of a diagonal of the regular hexagons.

The mesh plate is formed to have a multiplicity of minute holes. In the process for manufacturing the mesh plate, at the time of delivery and at other necessary times, inspection is required in order to determine whether the minute holes have been formed to the stipulated size and shape. Since it is virtually impossible to measure the diameters of all of the minute holes in this inspection, only specific minute holes are inspected. Since a change in the positions of minute holes to be inspected from one inspection to the next is undesirable, it is required that minute holes located at specific positions at all times be examined. If the blank portions 43 are provided as set forth above, minute holes that are to be examined can be determined using the blank portions 43 as a reference. For example, minute holes adjacent to and located on the outer side of the blank portions 43 may be examined. In this way the minute holes to undergo examination can be specified.

The other feature is that at least two types of cut-outs 44A, 44B of different size are formed at two respective locations (positions having point symmetry about the center of the mesh plate are excluded) on the periphery of the mesh plate 14. As will be described later, the mesh plate 14 has a front surface and a back surface (or a top surface and a bottom surface), and the mesh plate 14 must be installed in the cap 15 in such a manner that one surface of the mesh plate comes into surface contact with the upper end face of the horn 21A. Projections 57A, 57B of different size are provided on the step portion 57 of the base 52 of cap 15 and mate perfectly with the cut-outs 44A, 44B, respectively, of the mesh plate 14 when the mesh plate 14 has been placed in the correct surface orientation. If the cut-outs 44A, 44B are situated so as to mate with the projections 57A, 57B, the mesh plate 14 will be installed in the cap 15 with its surfaces pointing in the correct directions.

Figure 5:
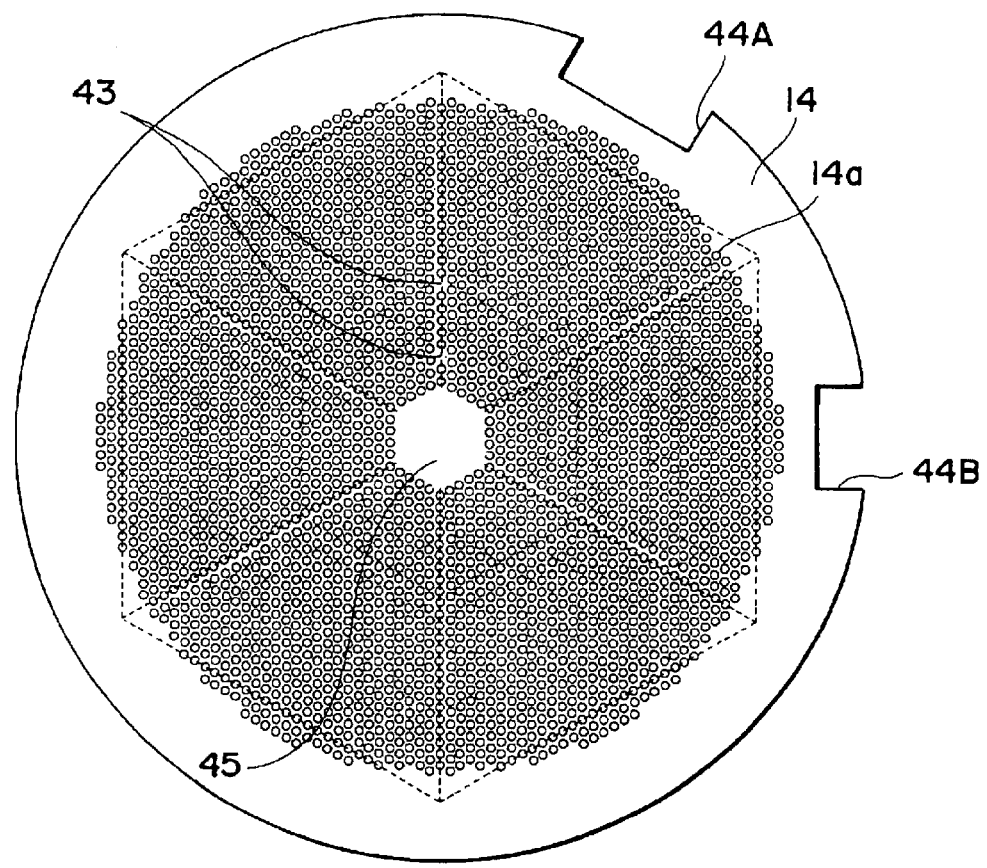
FIG. 5 is an enlarged plan view showing yet another example of a mesh plate.

A mesh plate 14 illustrated in FIG. 5 has still another characterizing feature. This is the fact that a comparatively large closed portion 45 is provided at the center of the mesh plate 14. No minute holes are formed in the closed portion 45. When the cap 15 having the mesh plate 14 installed therein has been fitted on the housing 10, the closed portion 45 opposes the opening in the pump bore 22 open at the upper end face of the horn 21A and acts to periodically close the opening as the opening vibrates. As a result, the valve action (described below) of the mesh plate 14 is reinforced so that more efficient pumping and spraying can be expected. The closed portion 45 should be large enough to close the opening in the upper end of the horn 21A. However, since the substantial area over which the minute holes may be provided is decreased if the closed portion is made too large, the closed portion should be sized so as not to have a deleterious effect upon the atomizing action. It goes without saying that in a case where the opening in the upper end of the horn 21A is not at the center but is offset to one side, the closed portion 45 also is provided in the mesh plate 14 at a position offset from the center thereof so that it will oppose the opening in the upper end of the horn.

Figure 6:
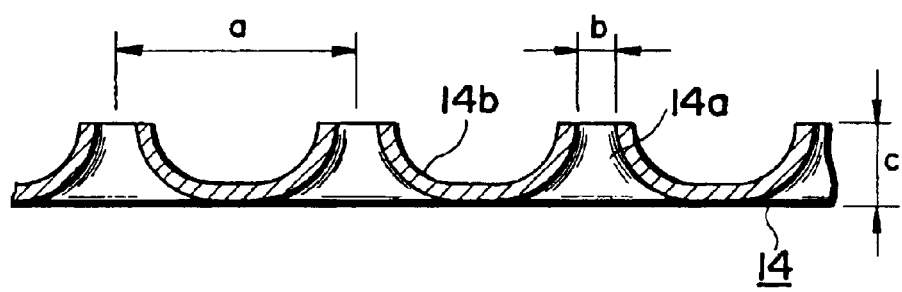
FIG. 6 is an enlarged sectional view showing a portion of a mesh plate.

FIG. 6 illustrates a portion of the cross section of the mesh plate in enlarged form.

The diameter of the circular minute holes 14a is small at the top surface of the mesh plate 14. The holes become successively wider and the diameter successively larger toward the bottom surface of the mesh plate. A recess or groove 14b opening toward the top surface is formed on the periphery of each minute hole 14a, namely between the minute holes 14a. As a result, a shape is obtained in which the rim defining each minute hole 14a projects in the upward direction. The mesh plate 14 is installed in the cap 15 in such a manner that the bottom surface of the mesh plate 14 opposes the upper end face of the horn 21A while the top surface opposes the spraying port 51 of the cap 15. This mesh plate 14 is characterized in that a comparatively large strength is obtained without making the plate thick.

As for an example of the dimensions of the various portions constituting the mesh plate having the sectional configuration shown in FIG. 6, the pitch a, of the minute holes 14a is 50~150 μm (a pitch on the order of 100 μm is suitable), the diameter b of the opening of each minute hole 14a in the top surface is on the order of 4.5±1 μm, the thickness c of the mesh plate 14 is on the order of 30~100 μm (a thickness on the order of 50 μm is suitable). Such a mesh plate can be fabricated by combining photoetching and electroforming techniques. Specifically, a number of electrodes are formed on an insulative plate by photoetching so as to correspond to the positions of the centers of the recesses 14b. This plate is adopted as a first negative. Next, a first metal is deposited on the electrodes by electroforming in such a manner that mutually independent mountains are formed. The resulting plate is adopted as a second negative. A second metal is further built up uniformly on each mountain of the second negative by electroforming. If the second negative is then peeled off the deposited second metal, a mesh plate comprising the layer of the second metal will be obtained. If it is acceptable for the minute holes to be comparatively large, the mesh plate having the shape shown in FIG. 6 can be fabricated by press work or injection molding.

Figure 7:
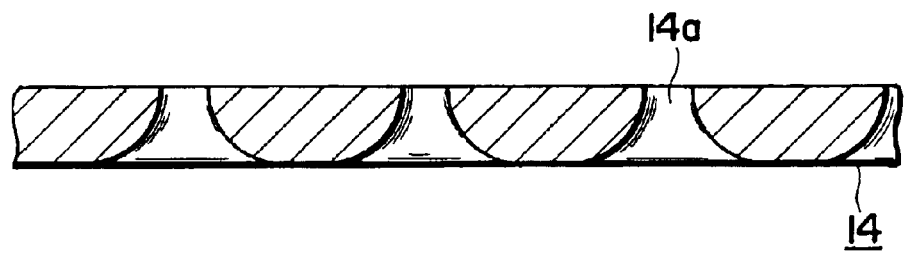
FIG. 7 is an enlarged sectional view showing a portion of another example of a mesh plate.

FIG. 7 shows another example of the mesh plate, in which the cross section is illustrated in enlarged form. Each of the multiplicity of minute holes 14a flares downwardly in such a manner that the diameter of the circular minute holes 14a is small at the top surface of the mesh plate 13 and becomes successively larger toward the bottom surface. Such a mesh plate is known in the art. The material may be metal or a plastic film. The minute holes need not be circular.

The directions in which the surfaces point when the mesh plate has been mounted in the cap is important because the diameters of the minute holes at the top surface and bottom surface differ.

Figure 8:
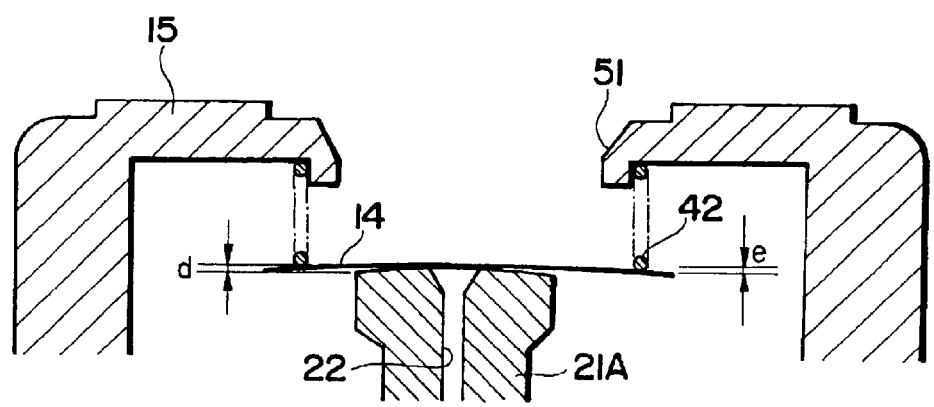
FIG. 8 is an enlarged sectional view showing a portion of a cap, a mesh plate and a horn.

FIG. 8 illustrates, in enlarged form, the shape of the upper end face of the horn 21A and the relationship among the mesh plate 14, the compression spring 42 and the cap 15.

The upper end face of the horn 21A is formed so as to be slightly and smoothly curved (spherically) in such a manner that the end face protrudes upwardly to the maximum extent at the center where the pump bore 22 opens. The mesh plate 14 is held fast at its periphery by the compression spring 42, as a result of which the mesh plate is caused to flex slightly. By way of example, the difference d between the highest and lowest points of the upper end face of the horn 21A is on the order of 20~50 μm, the amount of flexure of the mesh plate 14 is on the order of 5~10 μm, and the degree of curvature of the upper end face of the horn 21A is greater than the degree of curvature of the mesh plate 14 caused by flexing. It is important that the vicinity of the opening to the pump bore 22 in the upper end face of the horn be pressed by the mesh plate under the force of the compression spring 42. The degree of curvature of the upper end face of the horn, the strength of the mesh plate and the spring force of the compression spring are selected so as to produce this relationship.

The vertical (up-and-down) vibration of the horn 12A is accompanied by up-and-down vibration of the mesh plate 14, as mentioned above. Though the minute holes 14a are formed in the mesh plate 14, overall the mesh plate 14 acts as a valve which, by vibrating, opens and closes the opening in the upper end of the pump bore 22. Owing to this valve action of the mesh plate 14, liquid pumped up from the pump bore spreads over the upper end face of the horn 21A to form a liquid film when the valve is opened. When the valve is closed, the pumping action is suppressed and the above-mentioned liquid film is atomized through the mesh plate 14. In other words, pumping and atomization are performed alternately so that the amount of liquid pumped and the amount of liquid atomized balance each other, whereby an efficient, stabilized spraying action is achieved. According to tests and experiments carried out by the inventors, a spraying operation exhibiting stable performance was achieved. At present the reasons are believed to be as set forth above. With a mesh plate having the closed portion 45, as shown in FIG. 5, the above-described valve operation can be expected to be attained with even greater efficiency. The pumping effect produced by the valve action of the mesh plate is particularly important at the beginning of the spraying operation.

Figure 9:
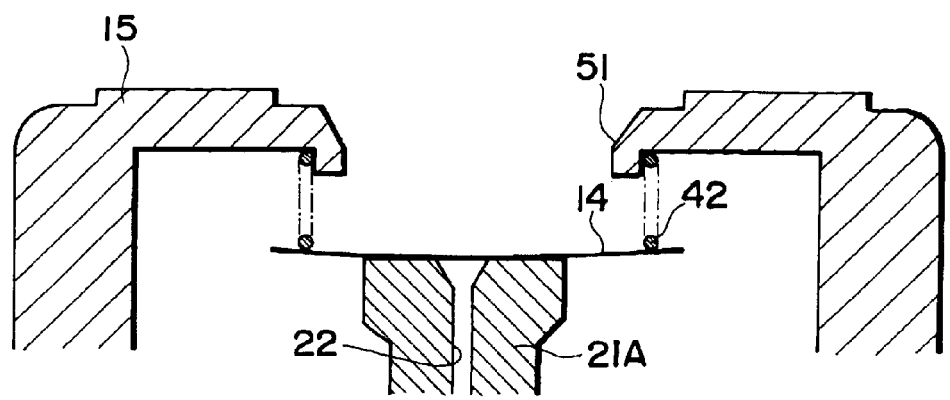
FIG. 9 is an enlarged sectional view showing another example of a portion of a cap, a mesh plate and a horn.
Figure 11:
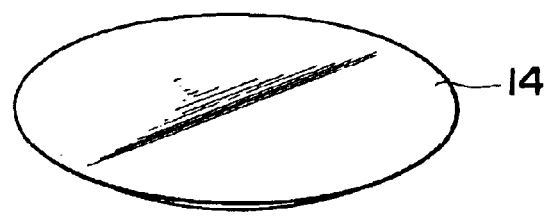
FIG. 11 is a perspective view showing another example of a mesh plate.
Figure 12A:
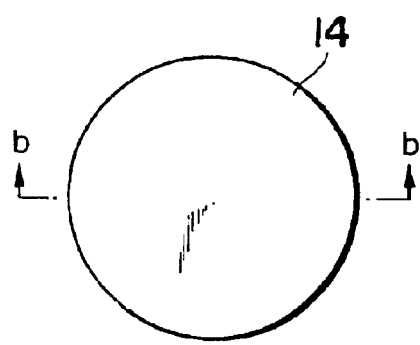
Figure 12C:
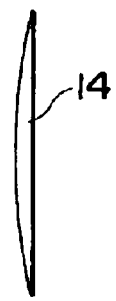
Figure 12B:

FIG. 9 illustrates another embodiment. Here the upper end face of the horn 21A is flat and the mesh plate 14 is curved so as to project downward. FIG. 11 is a perspective view of the mesh plate 14. Another example of a mesh plate usable in the arrangement shown in FIG. 9 is illustrated in FIGS. 12a through 12c. Here the mesh plate 14 is folded slightly and smoothly along a boundary which is a straight line passing through the center of the mesh plate. The minute holes are deleted from the illustrations in FIG. 11 and in FIGS. 12a through 12c.

Figure 10:
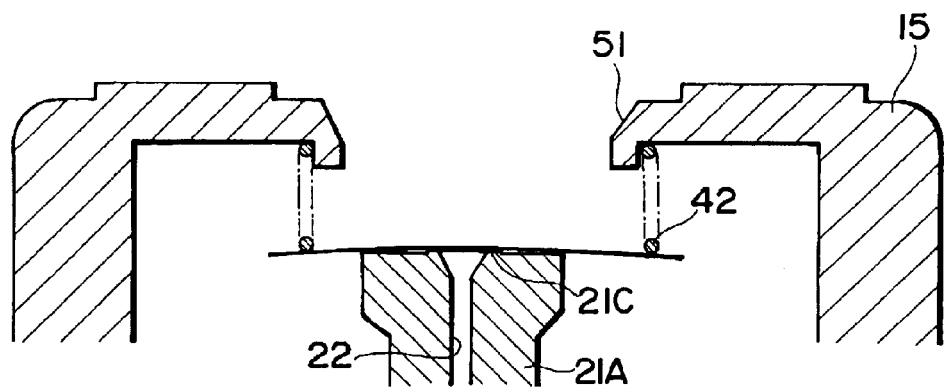
FIG. 10 is an enlarged sectional view showing yet another example of a portion of a cap, a mesh plate and a horn.

FIG. 10 illustrates yet another embodiment. Here the portion of the upper end face of horn 21A surrounding the opening in the upper end of the pump bore 22 protrudes slightly (the protruding portion is indicated at 21C).

In all of the examples described above, the diameter of the coil compression spring is set to be the same at all portions. The arrangement is such that the compression spring urges the periphery of the mesh plate extending outwardly of the upper end face of the horn. As a consequence, the mesh plate is caused to curve into an upwardly directed projection, and hence there is the possibility that the mesh plate will not be able to close off the opening in the upper end of the pump bore. In order to arrange it so that the opening in the upper end of the pump bore can be constrained by the mesh plate, the upper end face of the horn is curved so as to project upward, a projection is formed or the mesh plate is curved into a downwardly directly projection.

Figure 13:
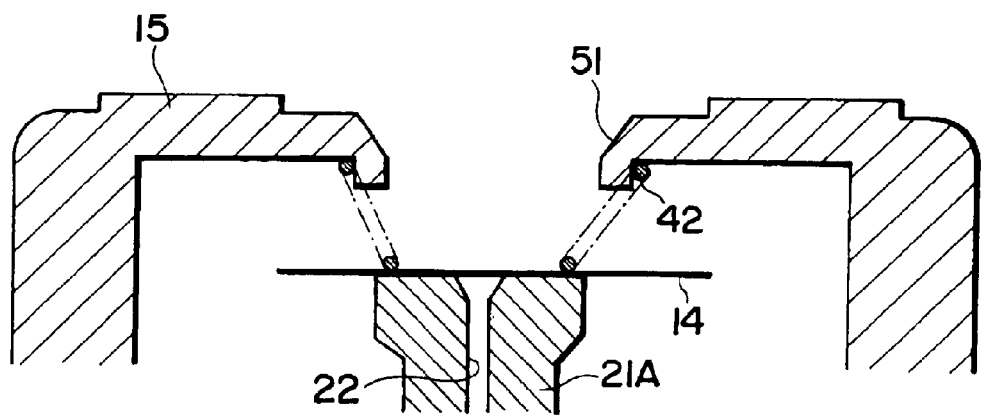
FIG. 13 is an enlarged sectional view showing another example of a compression spring.

By contrast, when a compression spring according to a modification shown in FIG. 13 is used, it is unnecessary to work the upper end face of the horn or the mesh plate. Here the upper end face of the horn is flat and the mesh plate 14 is flat as well. The compression spring 42 has a small diameter at its lower portion, with the diameter of the spring growing larger from the bottom to the top. The compression spring 42 urges the mesh plate 14 at the portion thereof on the upper end face of the horn 21A.

Figure 14:
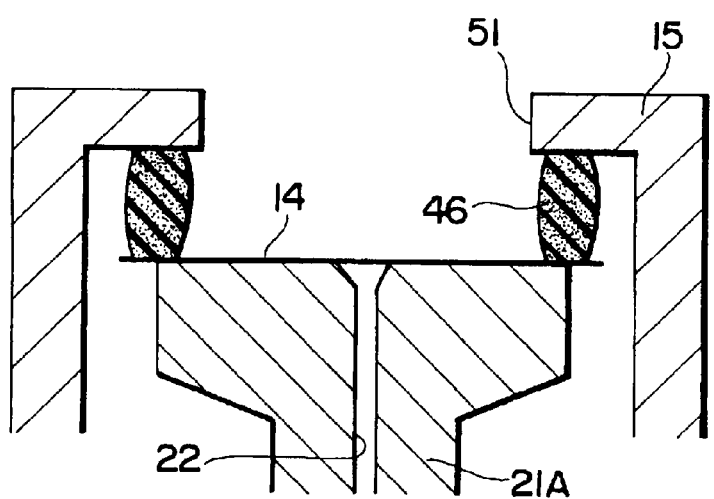
FIG. 14 is an enlarged sectional view showing another example of a biasing resilient member.

FIG. 14 illustrates another example of the biasing resilient member. Here an annular sponge 46 is used instead of the spring.

Figure 15:
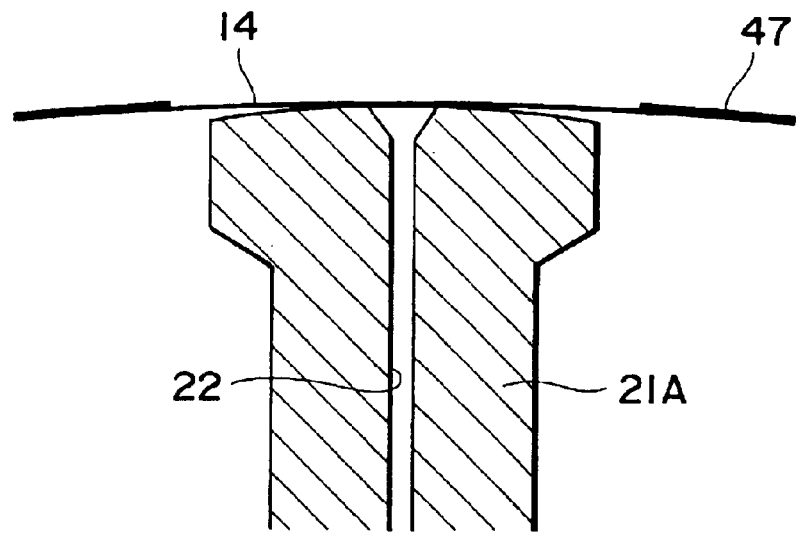
FIG. 15 is an enlarged sectional view showing an example in which an annular plate is attached to a mesh plate.

With the compression spring described above, the biasing force applied to the mesh plate will not necessarily be uniform. Accordingly, as shown in FIG. 15, it is recommended that an annular plate 47 simply be placed on the periphery of the mesh plate 14 or that the annular plate be fixed to periphery of the mesh plate 14 by bonding or welding, with the annular plate 47 being urged from above by the compression spring.

Figure 16:
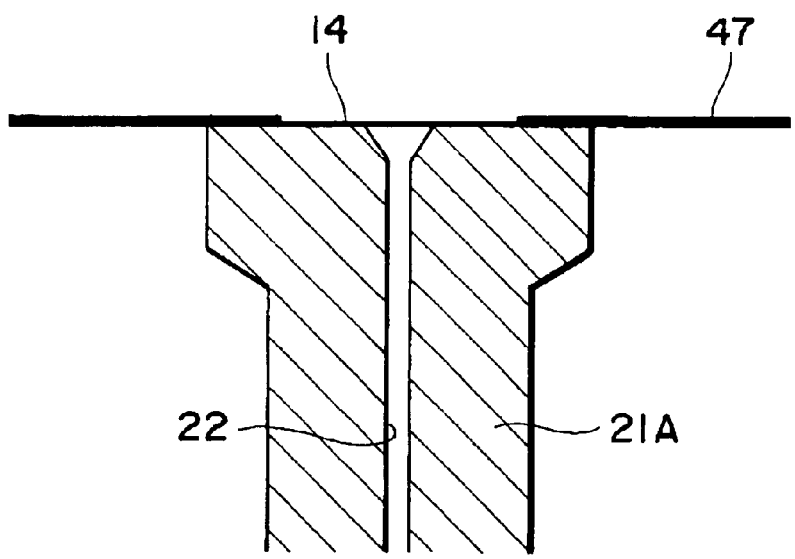
FIG. 16 is an enlarged sectional view showing another example in which an annular plate is attached to a mesh plate.

FIG. 16 shows an example in which the width of the annular plate 47 is enlarged so that the inner circumferential portion thereof engages the upper end face of the horn. In this case the upper end face of the horn 21A may be flat.

Figure 17:
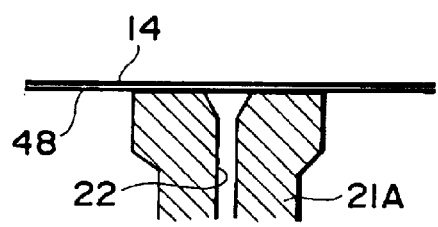
FIG. 17 is an enlarged sectional view showing an example in which a spacer is combined with a mesh plate.
Figure 18:
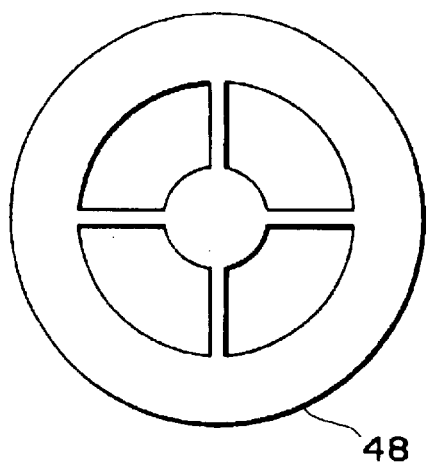
FIG. 18 is an enlarged plan view of the spacer.
Figure 19:
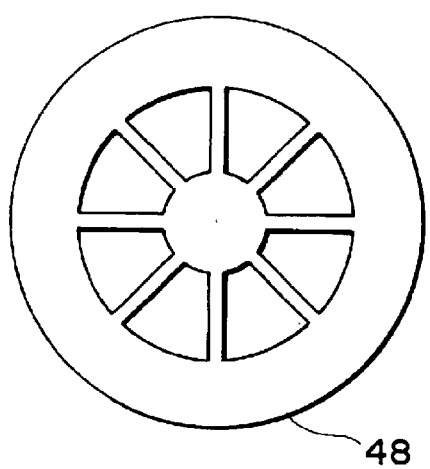
FIG. 19 is an enlarged plan view showing another example of a spacer.

FIG. 17 illustrates an example in which a spacer 48 instead of the annular plate 47 is interposed between the mesh plate 14 and the upper end face of the horn. As shown in FIG. 18 or 19, the spacer 48 is integrally formed to include a small circular portion at its center, an annular portion along its circumference and radiating connecting spokes connecting these two portions. The small circular portion at the center should be sized so as to cover the opening of the pump bore 22 in the upper end face of the horn. The upper end face of the horn 21A may be flat. The annular plate 47 and spacer 48 may both be made of metal or plastic.

Figure 20:
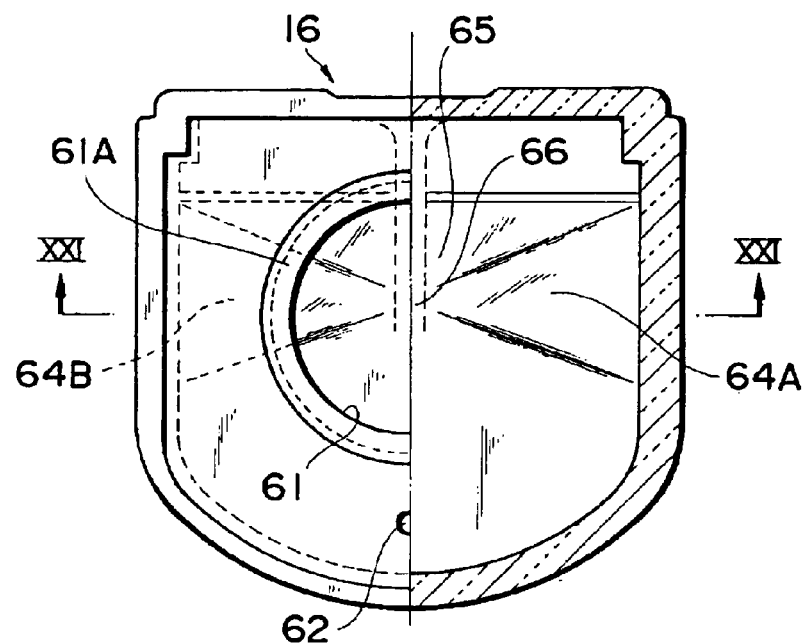
FIG. 20 is a partially cut-away plan view of a liquid vessel.
Figure 21:
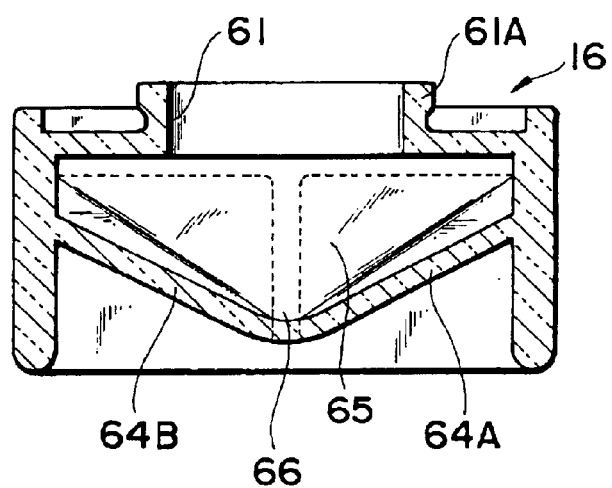
FIG. 21 is a sectional view taken along line XXI—XXI of FIG. 20.

The shape of the liquid vessel 16 will now be described with reference to FIGS. 2, 20 and 21.

The liquid vessel 16 has a rear wall 65 sloping downward toward the front. Further, both side portions 64A, 64B at the rear of a bottom wall 64 also slope upwardly toward the sides of the vessel. Since the principal mechanical portions of the ultrasonic atomizer are provided in an attitude in which they are inclined downwardly and forwardly, as shown in FIG. 1, the front portion of the bottom wall 64 is inclined downwardly and rearwardly in the state where the liquid vessel 16 is attached. In this way the liquid vessel 16 is formed to have its deepest recess 66, which is delimited by four inclined surfaces 64, 64A, 64B and 65. The lower end portion 21B of the pump shaft 21 is situated directly above the recess 66 in close proximity thereto and in fairly close proximity to the rear wall 65. By way of example, the distance between the lower end face of the pump shaft 21 and the bottom of the recess 66 is on the order of 2~3 mm, and the distance between the rear wall 65 and the part of the peripheral surface of the lower end of the pump shaft 21 that is nearest to the rear wall 65 is on the order of 1 mm.

In use of the ultrasonic atomizer, the liquid vessel 16 is filled with an appropriate amount of liquid, i.e., to such an extent that the liquid will not overflow. The liquid in the liquid vessel 16 decreases as the device is operated to spray the liquid. When the amount of liquid becomes small, the liquid collects in the deepest recess 66. When this occurs, a small amount of the liquid attaches itself to the lower end of the pump shaft 21, as shown at W in FIG. 2, and the liquid is pumped and sprayed to the last drop, owing to the energy of ultrasonic vibration (negative pressure) and the surface tension of the liquid. Thus, all of the liquid introduced to the interior of the liquid vessel 16 is used up without even a single drop being wasted. If the liquid is inexpensive, as in the case of water or a physiological saline solution, there is no particular inconvenience if some is left. If the liquid is a costly medicine, however, using up all of the liquid in the manner described above is economical since waste is avoided.

Figure 22:
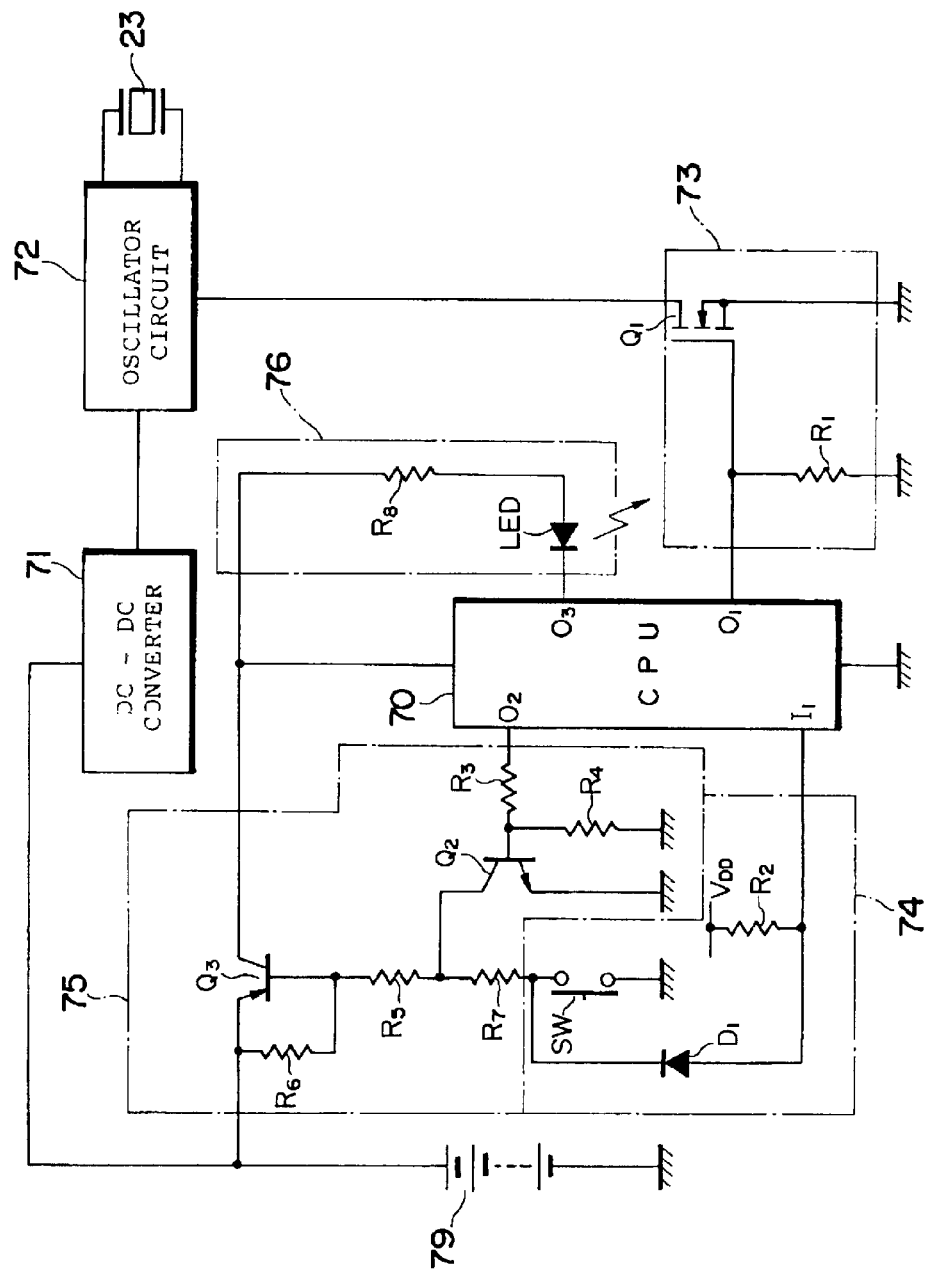
FIG. 22 is a circuit diagram showing an electric circuit of an ultrasonic atomizer.

Finally, the electrical construction of the ultrasonic atomizer will be described with reference to FIG. 22.

The electrical circuitry incorporated within the housing 10 of the ultrasonic atomizer comprises a CPU (microprocessor) 70 which controls overall operation, a DC/DC converter 71, an oscillator circuit (and drive circuit) 72, a gate circuit 73, a switch-status detecting circuit 74, a power-supply circuit 75, a display circuit 76 and a battery 79.

The operating voltage of the battery 79 is converted by the DC/DC converter 71 to a voltage suited to the operation of the oscillator circuit 72, and the converted voltage is applied to the oscillator circuit 72, which generates a high-frequency (ultrasonic) signal.

As will be described later, the oscillating operation of the oscillator circuit 72 is controlled by the CPU 70 via the gate circuit 73. The gate circuit 73 comprises a resistor $R_1$ and a MOS transistor $Q_1$. The starting and stopping of the oscillating operation of the oscillator circuit 72 is controlled in conformity with the voltage level (H level or L level) which the CPU 70 outputs from an output terminal $O_1$. When the oscillator circuit 72 operates, the output high-frequency signal is applied to the piezoelectric element 23 through a lead wire 25, whereby the ultrasonic pump 12 operates to perform atomization in the manner set forth above.

The switch-status detecting circuit 74 detects the on/off state of the switch SW operated by the user and applies the result of detection to the CPU 70. The operating switch SW is one type of push-button switch. The switch SW is ON during the time it is being pressed by the user and is turned off when the hand of the user is removed from the operating switch SW. The detecting circuit 74 comprises the operating switch SW, a diode $D_1$ and a pull-up resistor $R_2$. When the operating switch SW is turned on, an L-level voltage enters the CPU 70 from its input terminal $I_1$. If the switch is off, a high-level voltage enters the CPU 70 from its input terminal $I_1$.

The power-supply circuit 75 controls the supply of operating power from the battery 79 to the CPU 70. The power-supply circuit 75 comprises transistors Q2, Q3 and resistors R3, R4, R5, R6 and R7.

When the operating switch SW is turned on, the transistor Q3 turns on, as a result of which power is supplied to the CPU 70 through the transistor Q3. Operating power is supplied to the CPU 70 irrespective of the status of transistor Q2 as long as the switch SW is kept in the ON state.

Once operating power is supplied to the CPU 70, the CPU 70 continues to deliver an H-level ON signal to its output terminal $O_2$ except in a case where the supply of power is cut off under fixed conditions, as will be understood from a description given later. The transistor $Q_2$ is turned on by this H-level ON signal. Even if the operating switch SW is turned off, the transistor $Q_3$ is held in the ON state so that the CPU 70 continues to be supplied with operating power. When the CPU 70 judges that the power supply should be turned off, it inverts the output signal at the output terminal $O_2$ to the L level. When this is done, the transistor Q2 turns off and the transistor Q3 turns off as long as the switch SW is off. The supply of power to the CPU 70 is halted as a result. Thereafter, power is not supplied to the CPU 70 as long as the user does not turn on the switch SW.

The display circuit 76, which controls the lighting or flashing of a display device LED, includes a resistor $R_8$. The CPU 70 causes the L level to appear at an output terminal $O_3$ thereof in a case where the display device LED is lit. If the display device LED is to be flashed, the CPU outputs a pulse signal of a fixed period (e.g., 5 Hz) at its output terminal $O_3$. If the output terminal $O_3$ is at the H level, the display device LED remains extinguished. It goes without saying that lighting or flashing of the display device LED is performed only in a case where the transistor $Q_3$ is ON, thereby applying the operating voltage to the CPU 70 and display device LED.

According to this embodiment, there is a continuous-operation mode and an automatic intermittent-operation mode.

In the continuous-operation mode, the spraying operation proceeds in continuous fashion even if the operating switch SW is OFF. As shown in FIG. 26a, a transition is made to the continuous-operation mode when the operating switch SW is pressed continuously for more than four seconds. The transition is made to the continuous-operation mode also in a case where the operating switch SW is pressed continuously for more than four seconds when the automatic intermittent-operation mode (described next) is in effect and in the course of making a transition to the automatic intermittent-operation mode.

In the automatic intermittent-operation mode, the spraying operation and the halting thereof are repeated at a fixed period even if the operating switch SW is OFF. This period of intermittent spraying is decided by learning. As shown in FIG. 26b, a transition is made to the automatic intermittent-operation mode by having the user turn on the operating switch repeatedly three times, wherein the switch is turned on for less than four seconds each of the three times. In the course of this transition, the CPU 70 learns the period at which the operating switch is turned on and off (namely the ON time and the OFF time) and decides the period of intermittency (the ON/OFF repetition period) in the automatic intermittent-operation mode.

The automatic intermittent-operation mode is particularly effective in a case where the ultrasonic atomizer is applied to an inhaler. In an inhaler, atomized medicine is drawn in to the throat only when the user inhales. The medicinal inhalant used is expensive. In order to prevent wasteful use of the medicine, it is necessary to repeat the spraying operation and the termination thereof in conformity with the user's breathing. In the learning process, the period (time) at which the user turns the operating switch on and off is measured, whereby learning is performed. Even if the switch SW is not turned on and off after learning, the spraying operation and termination thereof are repeated automatically at a repetition period that conforms to the user's breathing. This is particularly useful for the elderly and children, who cannot perform the on/off operation skillfully.

If the operating switch SW is pressed again in the continuous-operation mode and automatic intermittent-operation mode and this ON time is less than four seconds, supply of power to the CPU 70 is halted (transistor $Q_2$ is turned off). Further, the power supply is turned off also in a case in which the switch SW is turned off for more than five seconds in the course of the transition to the automatic intermittent-operation mode (i.e., in the course of the learning process).

Figure 23:
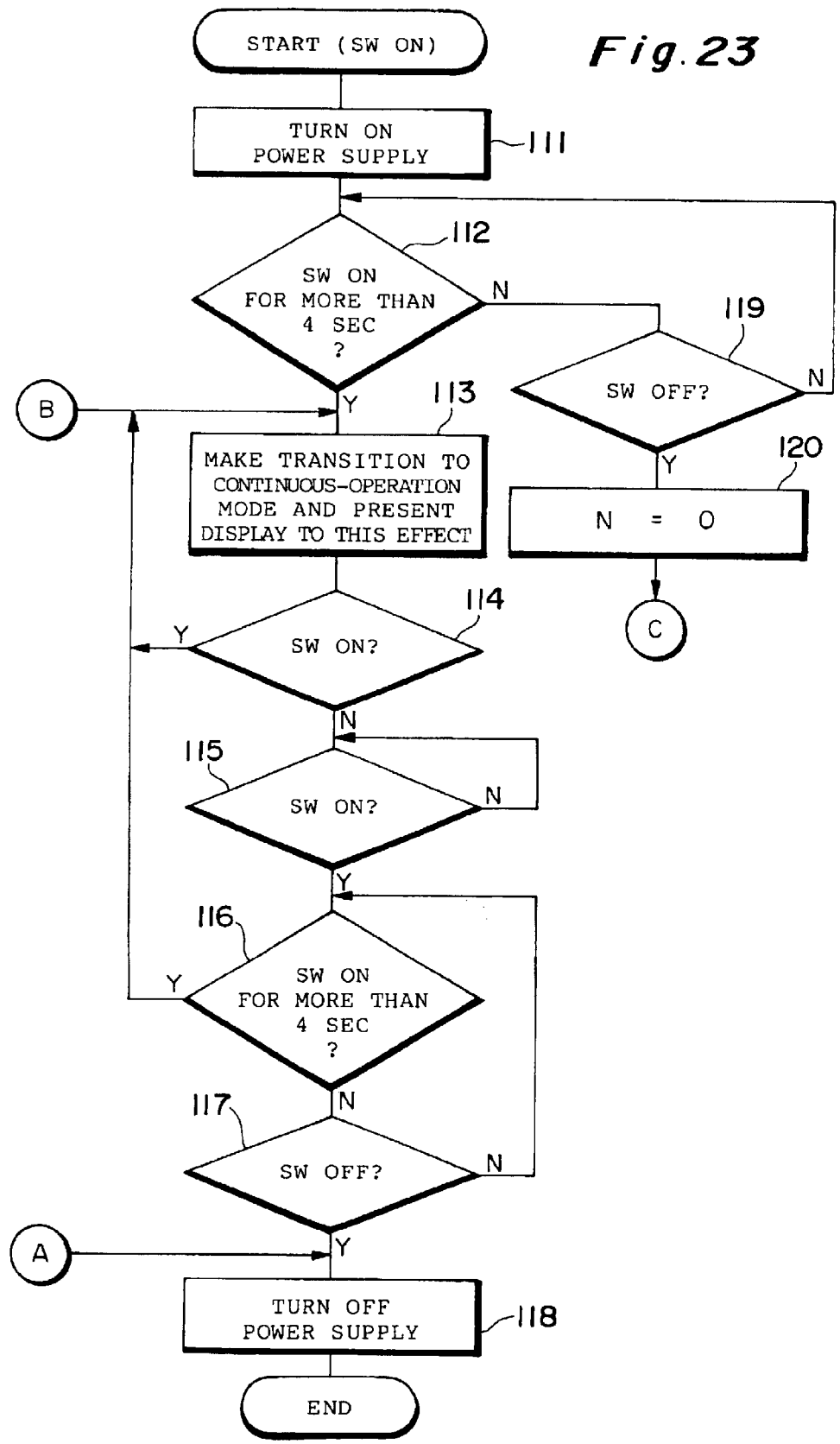
FIGS. 23 through 25 are flowcharts showing the processing procedure of a CPU.
Figure 24:
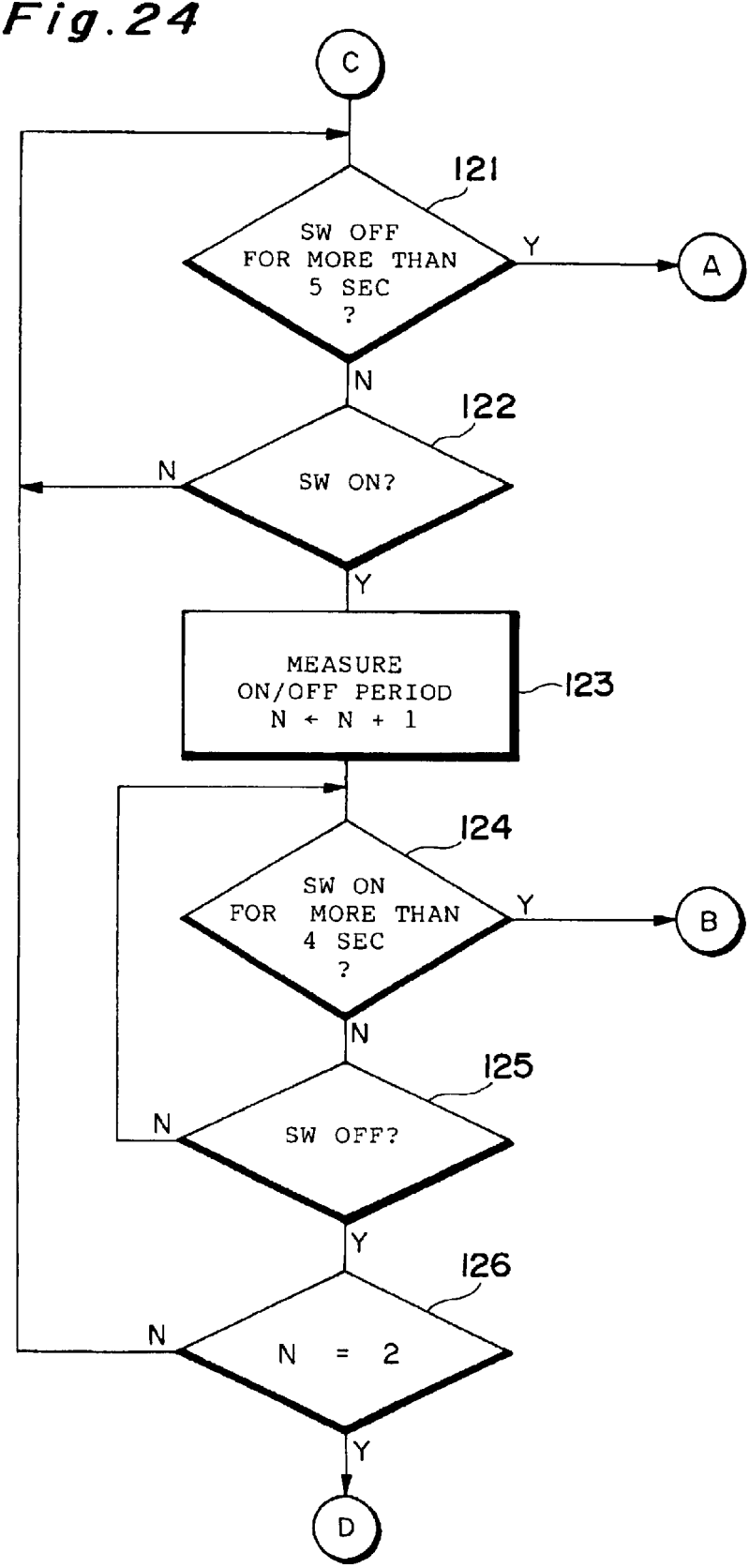
Figure 25:
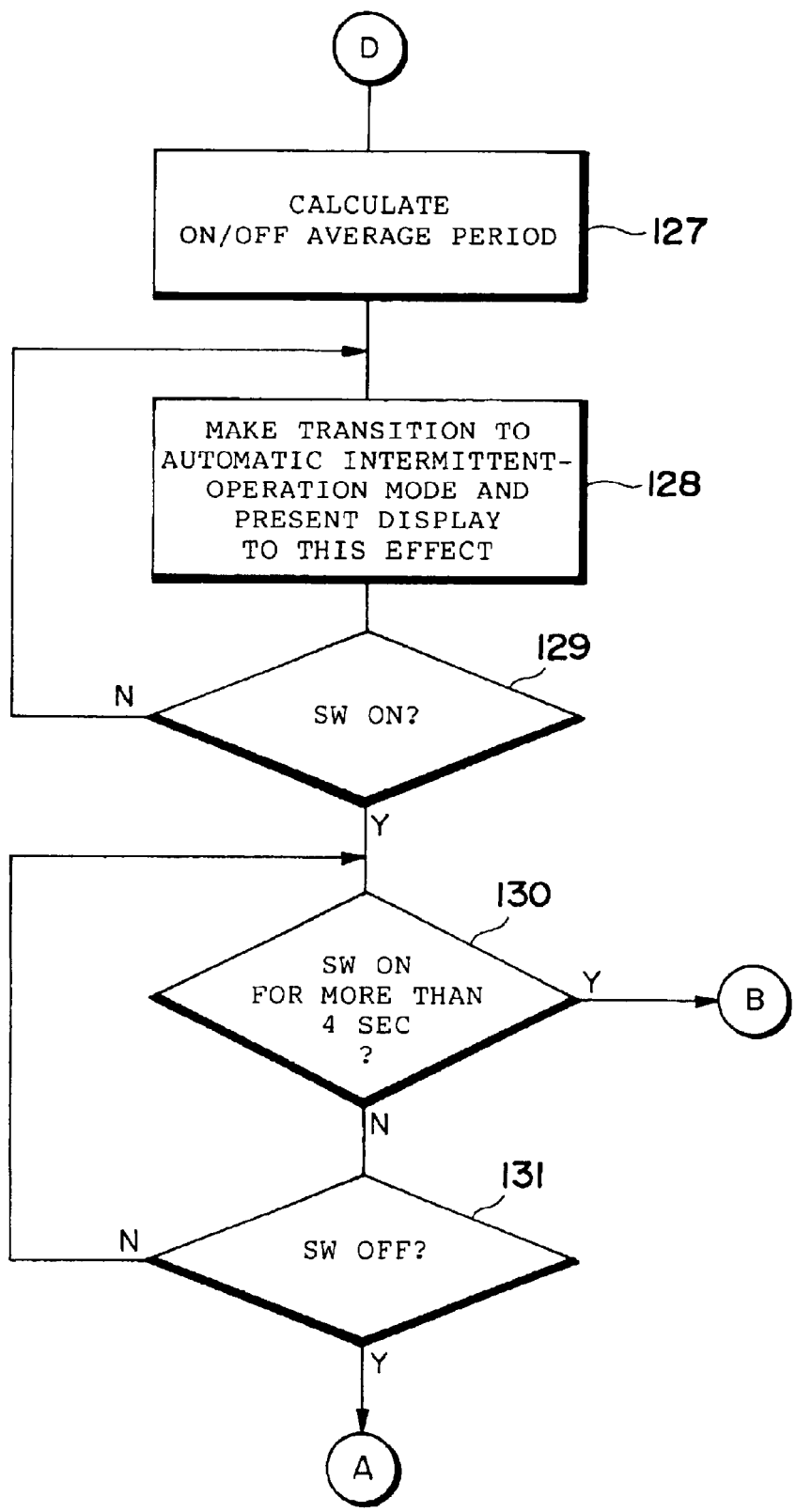

The flowcharts shown in FIGS. 23 through 25 illustrate the above-described operation in accordance with the processing procedure of the CPU 70.

The operation of the CPU 70 is started in response to the operating switch SW being turned on by the user. When the operating switch is turned on, the CPU 70 outputs an H-level signal at its output terminal $O_2$, thereby turning on the transistor $Q_2$ (step 111). As a result, the operating voltage is applied to the CPU 70 irrespective of the on/off operation of the switch SW, as described above.

If the operating switch SW is turned on continuously for more than four seconds (YES at step 112), a transition is made to the continuous-operation mode and a display to this effect is presented (step 113). After the operating switch SW has been kept in the ON state continuously for four seconds, the display device LED starts to flash and continues flashing until the switch is turned off, thereby indicating the fact that a transition has been made to the continuous-operation mode, as shown in FIG. 26a. The display device LED remains lit until elapse of four seconds from the moment the operating switch SW is turned on as well as during operation in the continuous-operation mode. The spraying operation is performed continuously from the moment the operating switch SW is turned on.

The spraying operation in the continuous-operation mode continues as long as the operating switch SW is not turned off subsequently (NO at step 114) and the operating switch SW is not turned on again (NO at step 115).

If the operating switch SW is turned on (YES at step 115) and this ON time is less than four seconds (NO at step 116 and YES at step 117), then the CPU 70 sends the output at its output terminal $O_2$ to the L level to cut off the supply of electric power (step 118).

In a case where the ON time of the operating switch SW is greater than four seconds (YES at step 116), then processing for a transition to the continuous-operation mode is performed again (step 113).

In a case where the operating switch SW is turned on and the ON time is less than four seconds (NO at step 112 and YES at step 119), a learning counter N is cleared (step 120).

When the operating switch SW is turned on again (YES at step 122), the results of the first learning operation, namely the results of measuring the preceding ON and OFF times of the switch, are accepted, one ON/OFF period is calculated and the learning counter N is incremented (step 122). The ON and OFF times of the switch SW are measured constantly by a timer or counter.

When the operating switch SW is turned off again less than four seconds after the switch has been turned on the second time (NO at step 124 and YES at step 125), the program returns to step 121 again if N=2 does not hold (NO at step 126), whereupon it is determined whether the switch SW has been turned on a third time (step 122).

When the operating switch SW is turned on the third time (YES at step 122), the results of measuring the second ON and OFF times of the switch SW are accepted, learning of the second ON/OFF period is performed and the counter N is incremented further (step 123).

When the operating switch SW is turned off again less than four seconds after the switch has been turned on the third time (NO at step 124 and YES at step 125), the average ON/OFF period is calculated (step 127) since the value in the learning counter N is already 2 (YES at step 126). That is, since the results of the second learning operation have already been stored, the average value of the ON time and the average value of the OFF time are calculated and these average values are decided on as the ON time and OFF time in the automatic intermittent-operation mode.

Thereafter, a transition is made to the automatic intermittent-operation mode, in which the spraying operation is performed intermittently at the period of the previously decided ON time and OFF time as long as the switch SW is OFF. Further, as shown in FIG. 26b, the display device LED flashes from the moment the operating switch SW is turned off the third time until the elapse of four seconds from the moment at which the operating switch SW was turned on the third time. This presents a display indicating that a transition is being made to the automatic intermittent-operation mode (step 128).

The display device LED is lit during the times that the operating switch SW is ON in the first through third operations thereof and when the spraying operation is being performed in the automatic intermittent-operation mode. Further, it goes without saying that the spraying operation also is carried out during the times that the operating switch SW is ON in the first through third operations thereof.

When the operating switch SW is subsequently turned on again for less than four seconds (YES at step 129, NO at step 130 and YES at step 131), the power supply is turned off (step 118).

In a case where the operating switch SW is turned off for more than five seconds in the course of making the transition to the automatic intermittent-operation mode (i.e., in the course of the learning operation) (YES at step 121), this is judged as indicating an erroneous operation or suspension of the operation; the power supply is turned off as a result (step 118).

In a case where the operating switch SW is turned on for more than four seconds in the course of the transition to the automatic intermittent-operation mode or in the automatic intermittent-operation mode (YES at step 124 and YES at step 130), an immediate transition is made to the continuous-operation mode (step 113).

In the embodiment described above, a learning operation is performed two times. However, it goes without saying that an arrangement may be adopted in which the ON time and OFF time of the operating switch SW are measured over a large number of times and the ON/OFF period in the automatic intermittent-operation mode is decided based upon the results.

Further, though a forcible transition to the automatic intermittent-operation mode is made when the operating switch SW is pressed three times (in which each ON time is less than four seconds) according to the foregoing embodiment, a manual mode may be provided in which the user is capable of turning the operating switch on and off at all times to control the intermittency of spraying in accordance with this ON/OFF operation. In order to distinguish between the manual mode and the automatic intermittent-operation mode, it can be so arranged that a transition is made to the automatic intermittent-operation mode only after the third ON operation of the operating switch is rendered intermittent for more than four seconds. Alternatively, a special switch for designating the automatic intermittent-operation mode can be provided. In this case also it goes without saying that learning can be performed one time or a plurality of times.

INDUSTRIAL APPLICABILITY

An automatic atomizer is applied in ultrasonic inhalers, by way of example. Ultrasonic inhalers are utilized in the medical-instrument industry.

What is claimed is:

1. An ultrasonic atomizer comprising:

an ultrasonic pump comprising a pump shaft formed to have a pump bore passing through it axially and having open upper and lower ends, and an ultrasonic vibrator mounted on the pump shaft in the vicinity of the midpoint thereof with respect to the axial direction;

a liquid vessel provided at a position at which it is penetrated by a lower end of said pump shaft;

a mesh plate placed on an upper end face of said pump shaft and formed to have a multiplicity of minute holes; and a biasing resilient member for biasing said mesh plate toward the upper end face of said pump shaft, wherein the upper end face of said pump shaft is formed to have a protuberance which projects in an area that includes the opening in the upper end of said pump bore.

2. An ultrasonic atomizer comprising:

an ultrasonic pump comprising a pump shaft formed to have a pump bore passing through it axially and having open upper and lower ends, and an ultrasonic vibrator mounted on the pump shaft in the vicinity of the midpoint thereof with respect to the axial direction;

a liquid vessel provided at a position at which it is penetrated by a lower end of said pump shaft;

a mesh plate placed on an upper end face of said pump shaft and formed to have a multiplicity of minute holes; and a biasing resilient member for biasing said mesh plate toward the upper end face of said pump shaft, wherein said mesh plate is formed to have a shape in which the central portion thereof is bent or curved slightly so as to point downward.

3. An ultrasonic atomizer comprising:

an ultrasonic pump comprising a pump shaft formed to have a pump bore passing through it axially and having open upper and lower ends, and an ultrasonic vibrator mounted on the pump shaft in the vicinity of the midpoint thereof with respect to the axial direction;

a liquid vessel provided at a position at which it is penetrated by a lower end of said pump shaft;

a mesh plate placed on an upper end face of said pump shaft and formed to have a multiplicity of minute holes; and a biasing resilient member for biasing said mesh plate toward the upper end face of said pump shaft, wherein said biasing resilient member is a compression coil spring having a coil diameter which becomes progressively smaller as said mesh plate is approached, in such a manner that said mesh plate is biased at a position thereof situated on the upper end face of said pump shaft.

4. A mesh plate used to produce an ultrasonic atomizing action, comprising a single plate-shaped body having two surfaces overall and formed to include a multiplicity of minute holes passing through the plate-shaped body from one surface to the other surface, said plate-shaped body being curved over its entire surface or folded and continuously deformed at the location of each minute hole in such a manner that each minute hole flares in a direction from the one surface to the other surface and a groove or recess is formed in said one surface between mutually adjacent ones of the minute holes.

5. An ultrasonic atomizer according to claim 4, wherein cut-outs of different size are formed in the periphery of said mesh plate at least at two locations other than locations having point symmetry about the center of said mesh plate.

6. An ultrasonic atomizer according to claim 4, wherein said minute holes are formed at equal intervals along sides of a multiplicity of regular hexagons whose diagonals vary at fixed distances.

7. An ultrasonic atomizer according to claim 4, wherein a small area devoid of formation of minute holes is present in an area surrounded by said minute holes.

8. An ultrasonic atomizer according to claim 4, wherein an area devoid of said minute holes is present at a central portion.

* * * * *